(12) United States Patent
Ding et al.

(10) Patent No.: US 12,146,937 B2
(45) Date of Patent: Nov. 19, 2024

(54) DISTANCE MEASUREMENT METHOD AND DISTANCE MEASUREMENT APPARATUS

(71) Applicant: HUAWEI TECHNOLOGIES CO., LTD., Guangdong (CN)

(72) Inventors: Genming Ding, Beijing (CN); Yanong He, Beijing (CN)

(73) Assignee: Huawei Technologies Co., Ltd., Shenzhen (CN)

( * ) Notice: Subject to any disclaimer, the term of this patent is extended or adjusted under 35 U.S.C. 154(b) by 318 days.

(21) Appl. No.: 17/842,931

(22) Filed: Jun. 17, 2022

(65) Prior Publication Data

US 2022/0326370 A1    Oct. 13, 2022

Related U.S. Application Data

(63) Continuation of application No. PCT/CN2020/137467, filed on Dec. 18, 2020.

(30) Foreign Application Priority Data

Dec. 18, 2019  (CN) .......................... 201911311965.1

(51) Int. Cl.
*G01S 13/34*     (2006.01)
*G01S 7/35*      (2006.01)
*H04B 17/318*    (2015.01)

(52) U.S. Cl.
CPC .............. *G01S 13/34* (2013.01); *G01S 7/354* (2013.01); *H04B 17/318* (2015.01)

(58) Field of Classification Search
CPC ........ G01S 13/34; G01S 7/357; H04B 17/318
See application file for complete search history.

(56) References Cited

U.S. PATENT DOCUMENTS 8,457,217 B2 *  6/2013  Phan Huy ........... H04L 25/0224
                                                  375/259
9,140,772 B1 *  9/2015  Dewberry ................ G01S 3/04
(Continued)

FOREIGN PATENT DOCUMENTS

CN          101136141 A       3/2008
CN          101598783 A      12/2009
                (Continued)

OTHER PUBLICATIONS

Extended European Search Report in European Appln No. 20902405.8, dated Dec. 15, 2022, 7 pages.
(Continued)

*Primary Examiner* — Peter M Bythrow
(74) *Attorney, Agent, or Firm* — Fish & Richardson P.C.

(57) ABSTRACT

The present disclosure relates to distance measurement methods and apparatuses. One example method includes receiving multiple first echo signals, determining multiple first spectrum data groups based on the multiple first echo signals, performing normalization processing on a signal strength value corresponding to each distance value comprised in each first spectrum data group to obtain a normalized signal strength value corresponding to each distance value, determining, based on a normalized signal strength value, a variance value of a signal strength value corresponding to each distance value comprised in the multiple first spectrum data groups, and determining a distance between a target obstacle on the to-be-measured object and the transmitting origin based on the variance value of the signal strength value corresponding to each distance value comprised in the multiple first spectrum data groups.

15 Claims, 12 Drawing Sheets

(56) References Cited

U.S. PATENT DOCUMENTS

| | | | | |
|---|---|---|---|---|
| 10,365,357 B2* | 7/2019 | Ebido | ............... | G01S 5/0036 |
| 10,674,474 B2* | 6/2020 | Poosamani | ......... | H04W 52/245 |
| 2015/0084807 A1* | 3/2015 | Nozawa | ............... | G01S 13/70 |
| | | | | 342/112 |
| 2018/0041985 A1* | 2/2018 | Davaadorj | .......... | H04W 64/003 |

FOREIGN PATENT DOCUMENTS

| | | | |
|---|---|---|---|
| CN | 103777199 | A | 5/2014 |
| CN | 107045120 | A | 8/2017 |
| CN | 207202887 | U | 4/2018 |
| CN | 108343769 | A | 7/2018 |
| CN | 109154651 | A | 1/2019 |
| IN | 110501719 | A | 11/2019 |
| JP | 2011127369 | A | 6/2011 |
| WO | 2018072598 | A1 | 4/2018 |
| WO | 2019071915 | A1 | 4/2019 |

OTHER PUBLICATIONS

PCT International Search Report and Written Opinion issued in International Application No. PCT/CN2020/137467 on Mar. 17, 2021, 19 pages (with English translation).

* cited by examiner

400

```
┌─────────────────────────────────────────────────────────────┐
│ Receive a plurality of first echo signals generated within  │
│ a first detection range by a plurality of first radar       │ ~ S410
│ signals transmitted in a first time segment                 │
└─────────────────────────────────────────────────────────────┘
                              ▼
┌─────────────────────────────────────────────────────────────┐
│ Determine, based on the plurality of first echo signals, a  │
│ plurality of first spectrum data groups corresponding to    │
│ the plurality of first echo signals, where each of the      │
│ plurality of first spectrum data groups includes a          │
│ plurality of pieces of first spectrum data, the plurality   │
│ of pieces of first spectrum data represent a plurality of   │
│ obstacle points within the first detection range, and       │
│ each of the plurality of pieces of first spectrum data      │
│ includes a distance value and a signal strength value;      │ ~ S420
│ the distance value in each piece of first spectrum data     │
│ is used to represent a distance between an obstacle point   │
│ represented by each piece of first spectrum data and a      │
│ first transmitting origin of the plurality of first radar   │
│ signals, the signal strength value in each piece of first   │
│ spectrum data is used to represent reflection strength      │
│ that is of a first radar signal corresponding to each piece │
│ of first spectrum data and that is at the obstacle point    │
│ represented by each piece of first spectrum data, and a     │
│ plurality of distance values included in each first         │
│ spectrum data group are the same                            │
└─────────────────────────────────────────────────────────────┘
                              ▼
┌─────────────────────────────────────────────────────────────┐
│ Perform normalization processing on a signal strength value │
│ corresponding to each of the plurality of distance values   │
│ included in each first spectrum data group, to obtain a     │ ~ S430
│ normalized signal strength value corresponding to each of   │
│ the plurality of distance values included in each first     │
│ spectrum data group                                         │
└─────────────────────────────────────────────────────────────┘
                              ▼
┌─────────────────────────────────────────────────────────────┐
│ Determine a first distance between a reference object at a  │
│ fixed position and the first transmitting origin based on a │
│ normalized signal strength value corresponding to a same    │ ~ S440
│ distance value in the plurality of first spectrum data      │
│ groups, where the first distance is greater than a distance │
│ between a to-be-measured object and the first transmitting  │
│ origin                                                      │
└─────────────────────────────────────────────────────────────┘
                              ▼
┌─────────────────────────────────────────────────────────────┐
│ Determine the distance between the to-be-measured object    │
│ and the first transmitting origin based on the first        │ ~ S450
│ distance                                                    │
└─────────────────────────────────────────────────────────────┘
```

FIG. 16

DISTANCE MEASUREMENT METHOD AND DISTANCE MEASUREMENT APPARATUS

CROSS-REFERENCE TO RELATED APPLICATIONS

This application is a continuation of International Application No. PCT/CN2020/137467, filed on Dec. 18, 2020, which claims priority to Chinese Patent Application No. 201911311965.1, filed on Dec. 18, 2019. The disclosures of the aforementioned applications are hereby incorporated by reference in their entireties.

TECHNICAL FIELD

This application relates to the field of sensor technologies, and more specifically, to a distance measurement method and a distance measurement apparatus in the field of sensor technologies.

BACKGROUND

With development of society and advancement of science and technology, sensor technologies are increasingly more widely used in distance measurement. For example, a height measurement apparatus is a distance measurement apparatus that can measure a height of a person. A health condition of a body is comprehensively evaluated based on a height obtained by a user by using the height measurement apparatus, in combination with physiological parameters such as a weight and body fat.

Existing 60 GHz and 77 GHz millimeter wave frequency bands have large available bandwidth. A frequency modulated continuous wave (FMCW) modulation mode may be used to achieve centimeter-level distance measurement precision, and may be used to perform speed measurement. At present, the FMCW modulation mode is widely used in a vehicle-mounted radar, to detect a distance of an obstacle and sense a distance of an object.

However, when a distance of a target is measured by using a distance measurement method using radar signals of different existing frequency bands, because the radar signals are easily affected by an obstacle in a surrounding environment, a distance of a wrong target is detected. Therefore, measurement accuracy is relatively low.

SUMMARY

Embodiments of this application provide a distance measurement method and a distance measurement apparatus, to improve measurement accuracy.

According to a first aspect, an embodiment of this application provides a distance measurement method. The method includes:

receiving a plurality of first echo signals generated within a detection range by a plurality of first radar signals transmitted in a first time segment;

determining a first point cloud dataset based on the plurality of first echo signals, where the first point cloud dataset includes a plurality of pieces of first point cloud data, the plurality of pieces of first point cloud data are used to represent a plurality of obstacle points on a to-be-measured object within the detection range, and each of the plurality of pieces of first point cloud data includes a distance value, a rate value, and a signal-to-noise ratio value; the distance value in each piece of first point cloud data is used to represent a distance between an obstacle point represented by each piece of first point cloud data and a transmitting origin of the plurality of first radar signals, the rate value in each piece of first point cloud data is used to represent a motion rate that is of the obstacle point represented by each piece of first point cloud data and that is relative to the transmitting origin, and the signal-to-noise ratio value in each piece of first point cloud data is used to represent noise at the obstacle point represented by each piece of first point cloud data;

performing denoising on the first point cloud dataset based on the signal-to-noise ratio value and the rate value that are in each piece of first point cloud data included in the first point cloud dataset, to obtain a target dataset;

clustering, based on a distance value in each piece of first point cloud data included in the target dataset, first point cloud data included in the target dataset, to obtain at least one classification, where the at least one classification corresponds to at least one obstacle, and an obstacle point included in each of the at least one classification forms an obstacle corresponding to each classification; and determining a distance between the obstacle corresponding to each classification and the transmitting origin based on a distance value in each piece of first point cloud data included in each classification.

It should be noted that, in this embodiment of this application, "first", "second", and the like are only used to distinguish same terms in different time segments, and are irrelevant to a quantity, a type, or the like, unless otherwise specified.

It should be further noted that, in this embodiment of this application, only an example in which the to-be-measured object is a person, and a height of the to-be-measured person is measured by using a distance measurement apparatus is used for description. However, this embodiment of this application is not limited thereto.

It should be noted that, before the receiving a plurality of first echo signals generated within a detection range by a plurality of first radar signals transmitted in a first time segment, measurement preparation needs to be first performed on the to-be-measured object, that is, a target obstacle disposed at an end that is of the to-be-measured object and that is farthest from the transmitting origin is slightly shaken.

For example, height measurement is used as an example, and the to-be-measured person needs to extend a palm out of a forehead and slightly shake the palm.

It should be noted that, because rates at obstacle points in different motion statuses are different, a rate at an obstacle point that forms the target obstacle shaking at the top of a head of the to-be-measured person is different from a rate at another surrounding obstacle point.

In a possible implementation, the performing denoising on the first point cloud dataset based on the signal-to-noise ratio value and the rate value that are in each piece of first point cloud data included in the first point cloud dataset, to obtain a target dataset includes: performing denoising on the first point cloud dataset based on the signal-to-noise ratio value and the rate value that are in each piece of first point cloud data included in the first point cloud dataset, a preset signal-to-noise ratio threshold, and a preset rate threshold, to obtain the target dataset, where the rate threshold is determined based on a rate of a target obstacle in the at least one obstacle.

It should be noted that a reflector with rate information is extracted to the first point cloud data in the distance measurement method in this embodiment of this application, and when rate resolution of a radar reaches 0.08 m/s, the radar can identify an obstacle with a slight vibration, for example, a slight vibration of a trunk when a body is in a static state. First point cloud data formed by such a vibrating object interferes with distance measurement of the target obstacle and needs to be filtered out. Therefore, interference may be filtered out by using the rate threshold.

In addition, in the distance measurement method in this embodiment of this application, slight shaking of the target obstacle is detected. Strength of an echo signal generated by such slight shaking is relatively weak, and a signal-to-noise ratio is not high. Therefore, noise may be filtered out by using the signal-to-noise ratio threshold.

In a possible implementation, the rate of the target obstacle is greater than or equal to the rate threshold.

It should be noted that the at least one obstacle obtained through clustering includes the target obstacle, the target obstacle includes a first obstacle point and a second obstacle point, and a distance between the first obstacle point and the second obstacle point is less than a preset distance threshold.

Optionally, the first point cloud data in the target first point cloud dataset may be clustered by using density-based spatial clustering of applications with noise.

In a possible implementation, the target obstacle includes a first obstacle point and a second obstacle point, and a distance between the first obstacle point and the second obstacle point is less than a preset distance threshold.

In a possible implementation, the target obstacle corresponds to a target classification in the at least one classification, and the determining a distance between the obstacle corresponding to each classification and the transmitting origin based on a distance value in each piece of first point cloud data included in each classification includes: determining a classification that includes a largest amount of first point cloud data in the at least one classification as the target classification and determining a distance between the target obstacle and the transmitting origin based on a distance value in each piece of first point cloud data included in the target classification.

It should be noted that the at least one classification includes the target classification corresponding to the target obstacle. Height measurement is used as an example, the target obstacle is disposed at the top of a head of a to-be-measured person, and the distance between the target obstacle and the transmitting origin may be understood as a height of the to-be-measured person.

According to the distance measurement method in this embodiment of this application, clustering the first point cloud data in the target first point cloud dataset and selecting the target classification help further eliminate interference caused by an outlier. The outlier comes from environmental interference other than the target obstacle, and also comes from an estimation error of a signal parameter generated by shaking of the target obstacle, such as deviations of coordinates x and y caused by an angle estimation error, and these parameters are to be used for distance measurement in a next step. Therefore, interference from an interfering point can be further reduced through clustering, thereby improving accuracy of distance measurement.

In a possible implementation, the distance value in each piece of first point cloud data includes a distance component value in a first direction and a distance component value in a second direction that are of the obstacle point represented by each piece of first point cloud data, where the first direction is perpendicular to the second direction; or the distance value in each piece of first point cloud data includes the distance component value in the first direction, the distance component value in the second direction, and a distance component value in a third direction that are of the obstacle point represented by each piece of first point cloud data, where the third direction is separately perpendicular to the first direction and the second direction.

In a possible implementation, the determining a first point cloud dataset based on the plurality of first echo signals includes: determining, based on the plurality of first echo signals, a plurality of first spectrum data groups corresponding to the plurality of first echo signals, where each of the plurality of first spectrum data groups includes a plurality of pieces of first spectrum data, the plurality of pieces of first spectrum data represent the plurality of obstacle points within the detection range, and each of the plurality of pieces of first spectrum data includes a distance value and a signal strength value; the distance value in each piece of first spectrum data is used to represent a distance between an obstacle point represented by each piece of first spectrum data and the transmitting origin, the signal strength value in each piece of first spectrum data is used to represent reflection strength that is of a first radar signal corresponding to each piece of first spectrum data and that is at the obstacle point represented by each piece of first spectrum data, and a plurality of distance values included in each first spectrum data group are the same; and determining the first point cloud dataset based on the distance value and the signal strength value that are in each piece of first spectrum data.

In a possible implementation, before the determining the first point cloud dataset based on the distance value and the signal strength value that are in each piece of first spectrum data, the method further includes: receiving a plurality of second echo signals generated within the detection range by a plurality of second radar signals transmitted in a second time segment, where an end time point of the second time segment is not later than an end time point of the first time segment; determining, based on the plurality of second echo signals, a plurality of second spectrum data groups corresponding to the plurality of second echo signals, where each of the plurality of second spectrum data groups includes a plurality of pieces of second spectrum data, the plurality of pieces of second spectrum data represent the plurality of obstacle points within the detection range, and each of the plurality of pieces of second spectrum data includes a distance value and a signal strength value; the distance value in each piece of second spectrum data is used to represent a distance between an obstacle point represented by each piece of second spectrum data and the transmitting origin, the signal strength value in each piece of second spectrum data is used to represent reflection strength that is of a second radar signal corresponding to each piece of second spectrum data and that is at the obstacle point represented by each piece of second spectrum data, and a plurality of distance values included in each second spectrum data group are the same; determining, based on the distance value and the signal strength value that are in each piece of second spectrum data, whether a position of the to-be-measured object meets a measurement condition; and determining the first point cloud dataset when determining that the position of the to-be-measured object meets the measurement condition.

It should be noted that, before determining the first point cloud dataset based on the distance value and the signal strength value that are in each piece of first spectrum data, the distance measurement apparatus may first determine whether the position of the to-be-measured object meets the measurement condition, and then perform distance measurement when the position of the to-be-measured object meets the measurement condition. When the position of the to-be-measured object does not meet the measurement condition, a distance measurement function may be suspended, to reduce energy consumption.

In a possible implementation, the determining, based on the distance value and the signal strength value that are in each piece of second spectrum data, whether a position of the to-be-measured object meets a measurement condition includes: performing normalization processing on a signal strength value corresponding to each of the plurality of distance values included in each second spectrum data group, to obtain a normalized signal strength value corresponding to each of the plurality of distance values included in each second spectrum data group; determining, based on a normalized signal strength value corresponding to a same distance value in the plurality of second spectrum data groups, a variance value of a signal strength value corresponding to each of the plurality of distance values; and determining, based on the variance value of the signal strength value corresponding to each of the plurality of distance values, whether the position of the to-be-measured object meets the measurement condition.

Optionally, that the end time point of the second time segment is not later than the end time point of the first time segment may include: The end time point of the second time segment is earlier than the end time point of the first time segment; or the end time point of the second time segment is equal to the end time point of the first time segment. This is not limited in this embodiment of this application.

Optionally, duration of the second time segment may be the same as or different from duration of the first time segment. This is not limited in this embodiment of this application.

In a possible implementation, the determining, based on the variance value of the signal strength value corresponding to each of the plurality of distance values, whether the position of the to-be-measured object meets the measurement condition includes: when a quantity of variance values that are greater than a variance threshold and that are of signal strength values corresponding to all of the plurality of distance values is greater than or equal to a quantity threshold, determining that the position of the to-be-measured object meets the measurement condition; or when the quantity of variance values that are greater than the variance threshold and that are of signal strength values corresponding to all of the plurality of distance values is less than the quantity threshold, determining that the position of the to-be-measured object does not meet the measurement condition.

According to the distance measurement method provided in this embodiment of this application, it is not necessary to use an external sensor such as a human body infrared sensor or a pressure sensor to determine whether the distance measurement function may be started, thereby simplifying the measurement apparatus, and reducing power consumption and costs.

It should be noted that height measurement is used as an example, and an instantaneous height value obtained by using the method in the first aspect is affected by noise interference, hand lifting, hand falling, a slight trunk vibration, and the like, causing a large change in the instantaneous value. Therefore, accuracy and stability of a measured height value may be improved by using the following two methods.

Method 1: Statistics on a variance $\sigma_k^2$ of an instantaneous height value measured at each of consecutive frame time points within 1s are collected. If of $\sigma_k^2 \leq \sigma_{th1}$, an average value of instantaneous height values measured at all frames within 1s is used as a final height value of a to-be-measured person. $\sigma_{th1}$ is a preset first variance threshold, and a value range of the first variance threshold is a first threshold range.

Method 2: Statistics on a variance $\sigma_h^2$ of an instantaneous height value obtained at each of consecutive frame time points in a plurality of seconds are collected. If $\sigma_h^2 \leq \sigma_{th2}$, a height value interval with most concentrated distribution is extracted by using histogram distribution, and then an average value of height values included in the interval is used as a final height value of a to-be-measured person. $\sigma_{th2}$ is a preset second variance threshold, and a value range of the second variance threshold is a second threshold range. The second threshold range is greater than the first threshold range.

According to a second aspect, an embodiment of this application further provides a distance measurement method. The method includes:

receiving a plurality of first echo signals generated within a detection range by a plurality of first radar signals transmitted in a first time segment;

determining, based on the plurality of first echo signals, a plurality of first spectrum data groups corresponding to the plurality of first echo signals, where each of the plurality of first spectrum data groups includes a plurality of pieces of first spectrum data, the plurality of pieces of first spectrum data represent a plurality of obstacle points on a to-be-measured object within the detection range, and each of the plurality of pieces of first spectrum data includes a distance value and a signal strength value; the distance value in each piece of first spectrum data is used to represent a distance between an obstacle point represented by each piece of first spectrum data and a transmitting origin of the plurality of first radar signals, the signal strength value in each piece of first spectrum data is used to represent signal reflection strength at the obstacle point represented by each piece of first spectrum data, and a plurality of distance values included in each first spectrum data group are the same;

performing normalization processing on a signal strength value corresponding to each distance value included in each first spectrum data group, to obtain a normalized signal strength value corresponding to each distance value included in each first spectrum data group;

determining, based on a normalized signal strength value corresponding to a same distance value in the plurality of first spectrum data groups, a variance value of a signal strength value corresponding to each distance value included in the plurality of first spectrum data groups; and determining a distance between a target obstacle on the to-be-measured object and the transmitting origin based on the variance value of the signal strength value corresponding to each distance value included in the plurality of first spectrum data groups, where the target obstacle includes at least one obstacle point, and signal reflection strength at obstacle points in different motion statuses is different.

It should be noted that height measurement is used as an example, the target obstacle is disposed at the top of a head of a to-be-measured person, and the distance between the target obstacle and the transmitting origin may be understood as a height of the to-be-measured person.

It should be noted that height measurement is used as an example, and during measurement preparation, a user extends a palm and slightly shakes the palm at the top of a head, so that a variance value at a range-bin corresponding to a height of the top of the head is increased. Therefore, a distance value corresponding to a farthest wave peak that is in a Range-FFT variance curve spectrum and whose value is greater than or equal to a variance threshold is searched for within a distance threshold range and is used as a current instantaneous height value; or a largest distance value whose variance is greater than or equal to the variance threshold is used as the current instantaneous height value.

In a possible implementation, the determining a distance between a target obstacle on the to-be-measured object and the transmitting origin based on the variance value of the signal strength value corresponding to each distance value included in the plurality of first spectrum data groups includes: determining the distance between the target obstacle and the transmitting origin based on the variance value of the signal strength value corresponding to each distance value included in the plurality of first spectrum data groups and a first variance threshold, where the first variance threshold is determined based on signal strength at the at least one obstacle point that forms the target obstacle.

In a possible implementation, before the performing normalization processing on a signal strength value corresponding to each distance value included in each first spectrum data group, to obtain a normalized signal strength value corresponding to each distance value included in each first spectrum data group, the method further includes: receiving a plurality of second echo signals generated within the detection range by a plurality of second radar signals transmitted in a second time segment, where an end time point of the second time segment is not later than an end time point of the first time segment; determining, based on the plurality of second echo signals, a plurality of second spectrum data groups corresponding to the plurality of second echo signals, where each of the plurality of second spectrum data groups includes a plurality of pieces of second spectrum data, the plurality of pieces of second spectrum data represent the plurality of obstacle points within the detection range, and each of the plurality of pieces of second spectrum data includes a distance value and a signal strength value; the distance value in each piece of second spectrum data is used to represent a distance between an obstacle point represented by each piece of second spectrum data and the transmitting origin, the signal strength value in each piece of second spectrum data is used to represent signal reflection strength at the obstacle point represented by each piece of second spectrum data, and a plurality of distance values included in each second spectrum data group are the same; determining, based on the distance value and the signal strength value that are in each piece of second spectrum data, whether a position of the to-be-measured object meets a measurement condition; and when determining that the position of the to-be-measured object meets the measurement condition, performing normalization processing on the signal strength value corresponding to each distance value included in each first spectrum data group.

In a possible implementation, the determining, based on the distance value and the signal strength value that are in each piece of second spectrum data, whether a position of the to-be-measured object meets a measurement condition includes: performing normalization processing on a signal strength value corresponding to each distance value included in each second spectrum data group, to obtain a normalized signal strength value corresponding to each distance value included in each second spectrum data group; determining, based on a normalized signal strength value corresponding to a same distance value in the plurality of second spectrum data groups, a variance value of a signal strength value corresponding to each distance value included in the plurality of second spectrum data groups; and determining, based on the variance value of the signal strength value corresponding to each distance value included in the plurality of second spectrum data groups, whether the position of the to-be-measured object meets the measurement condition.

In a possible implementation, the determining, based on the variance value of the signal strength value corresponding to each distance value included in the plurality of second spectrum data groups, whether the position of the to-be-measured object meets the measurement condition includes: when a quantity of variance values that are greater than a second variance threshold and that are of signal strength values corresponding to all distance values included in the plurality of second spectrum data groups is greater than or equal to a quantity threshold, determining that the position of the to-be-measured object meets the measurement condition; or when the quantity of variance values that are greater than the second variance threshold and that are of signal strength values corresponding to all distance values included in the plurality of second spectrum data groups is less than the quantity threshold, determining that the position of the to-be-measured object does not meet the measurement condition.

According to a third aspect, an embodiment of this application further provides a distance measurement method. The method includes:

receiving a plurality of first echo signals generated within a first detection range by a plurality of first radar signals transmitted in a first time segment;

determining, based on the plurality of first echo signals, a plurality of first spectrum data groups corresponding to the plurality of first echo signals, where each of the plurality of first spectrum data groups includes a plurality of pieces of first spectrum data, the plurality of pieces of first spectrum data represent a plurality of obstacle points within the first detection range, and each of the plurality of pieces of first spectrum data includes a distance value and a signal strength value; the distance value in each piece of first spectrum data is used to represent a distance between an obstacle point represented by each piece of first spectrum data and a first transmitting origin of the plurality of first radar signals, the signal strength value in each piece of first spectrum data is used to represent reflection strength that is of a first radar signal corresponding to each piece of first spectrum data and that is at the obstacle point represented by each piece of first spectrum data, and a plurality of distance values included in each first spectrum data group are the same;

performing normalization processing on a signal strength value corresponding to each of the plurality of distance values included in each first spectrum data group, to obtain a normalized signal strength value corresponding to each of the plurality of distance values included in each first spectrum data group;

determining a first distance between a reference object at a fixed position and the first transmitting origin based on a normalized signal strength value corresponding to a same distance value in the plurality of first spectrum data groups, where the first distance is greater than a distance between a to-be-measured object and the first transmitting origin; and determining the distance between the to-be-measured object and the first transmitting origin based on the first distance.

It should be noted that, because an amplitude at each range-bin in the normalized Range-FFT reflects reflection strength that is of a radar signal and that is at an obstacle point, a distance corresponding to a farthest wave peak that is in the normalized Range-FFT and whose amplitude is greater than an amplitude threshold may be considered as the first distance between the reference object and the first transmitting origin.

It should be noted that, when the first distance is measured, a detection direction of the first radar signal is from the first transmitting origin to the reference object, and because the first distance is irrelevant to the to-be-measured object, the first radar signal does not need to detect distance information of the to-be-measured object. Therefore, the to-be-measured object may be located at a position far from the first radar signal, or outside the detection range of the first radar signal. This is not limited in this embodiment of this application.

For example, height measurement is used as an example, the first distance may be a distance between a sole of a foot of a to-be-measured person and a ceiling, and a second distance may be a distance between atop of a head of the to-be-measured person and the ceiling.

Optionally, before the distance between the to-be-measured object and the first transmitting origin is determined based on the first distance, a second distance between the reference object and an end that is of the to-be-measured object and that is closest to the reference object may be obtained. The determining the distance between the to-be-measured object and the first transmitting origin based on the first distance includes: determining the distance between the to-be-measured object and the first transmitting origin based on the first distance and the second distance.

In a possible implementation, a plurality of second echo signals generated within a second detection range by a plurality of second radar signals transmitted in a second time segment may be received, where detection directions of the second detection range and the first detection range are opposite. A plurality of second spectrum data groups corresponding to the plurality of second echo signals are determined based on the plurality of second echo signals, where each of the plurality of second spectrum data groups includes a plurality of pieces of second spectrum data, the plurality of pieces of second spectrum data represent a plurality of obstacle points within the second detection range, and each of the plurality of pieces of second spectrum data includes a distance value and a signal strength value. The distance value in each piece of second spectrum data is used to represent a distance between an obstacle point represented by each piece of second spectrum data and a second transmitting origin of the plurality of second radar signals, the signal strength value in each piece of second spectrum data is used to represent reflection strength that is of the plurality of second radar signals and that is at the obstacle point represented by each piece of second spectrum data, and a plurality of distance values included in each second spectrum data group are the same. Normalization processing is performed on a signal strength value corresponding to each of the plurality of distance values included in each second spectrum data group, to obtain a normalized signal strength value corresponding to each of the plurality of distance values included in each second spectrum data group. The second distance is determined based on a normalized signal strength value corresponding to a same distance value in the plurality of second spectrum data groups.

It should be noted that a principle of a determining process of the second distance is similar to a principle of a determining process of the first distance, and a difference lies only in that the second distance is a distance between the reference object and the end that is of the to-be-measured object and that is closest to the reference object. Therefore, a distance measurement apparatus needs to be placed at the end closest to the reference object. That is, a detection direction of the second radar signal is opposite to the detection direction of the first radar signal, that is, is from the end closest to the reference object to the reference object.

It should be further noted that accuracy of distance measurement may be further improved by using the method for improving accuracy of distance measurement described in the first aspect, and whether a position of the to-be-measured object meets a measurement condition may be determined by using the method for determining whether a position of a to-be-measured object meets a measurement condition described in the first aspect. To avoid repetition, details are not described herein.

According to the distance measurement method provided in this embodiment of this application, distribution of an obstacle in a radar detection range can be better reflected, to facilitate setting of a unified threshold, thereby improving universality of an algorithm and a product.

According to a fourth aspect, an embodiment of this application further provides a distance measurement apparatus, configured to perform the methods in the foregoing aspects or any possible implementations of the foregoing aspects. Specifically, the distance measurement apparatus may include a unit configured to perform the methods in the foregoing aspects or any possible implementations of the foregoing aspects.

According to a fifth aspect, an embodiment of this application further provides a distance measurement apparatus. The apparatus includes a processor and a transceiver, and the processor and the transceiver communicate with each other by using an internal connection path. The processor is configured to implement the methods in the foregoing aspects or any possible implementations of the foregoing aspects.

According to a sixth aspect, an embodiment of this application further provides a computer-readable storage medium, configured to store a computer program. The computer program includes instructions used to implement the methods in the foregoing aspects or any possible implementations of the foregoing aspects.

According to an eighth aspect, an embodiment of this application further provides a computer program product including instructions. When the computer program product is run on a computer, the computer is enabled to implement the methods in the foregoing aspects or any possible implementations of the foregoing aspects.

According to a ninth aspect, an embodiment of this application further provides a chip apparatus, including a processor, and a communications interface. The processor and the communications interface communicate with each other by using an internal connection path, the communications interface is configured to communicate with an external component or an internal component, and the processor is configured to implement the methods in the foregoing aspects or any possible implementations of the foregoing aspects.

BRIEF DESCRIPTION OF DRAWINGS

FIG. 16 is a schematic flowchart of a distance measurement method 400 according to an embodiment of this application;

DESCRIPTION OF EMBODIMENTS

The following describes technical solutions in embodiments of this application with reference to accompanying drawings in the embodiments of this application.

Figure 1:
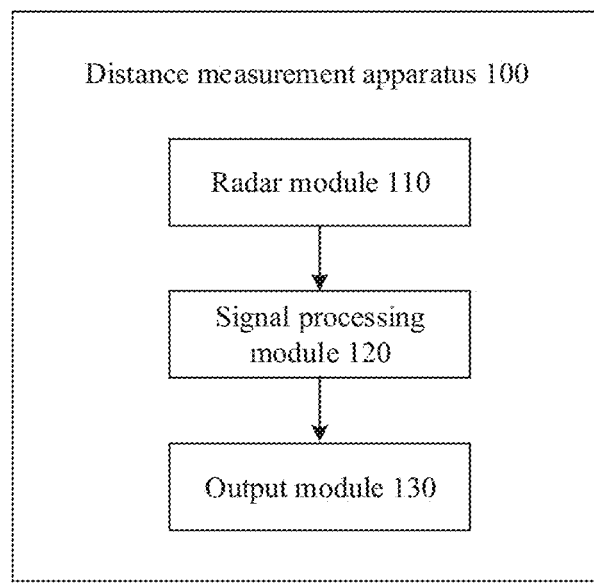
FIG. 1 is a schematic block diagram of a distance measurement apparatus 100 according to an embodiment of this application.

FIG. 1 shows a schematic block diagram of a distance measurement apparatus 100 according to an embodiment of this application. As shown in FIG. 1, the apparatus 100 includes a radar module 110, a signal processing module 120, and an output module 130.

The radar module 110 is configured to periodically transmit a radar signal, where the radar signal uses a frequency modulated continuous wave (FMCW) modulation mode, and receive an echo signal generated within a detection range by the radar signal, and send the received echo signal to the signal processing module 120.

It should be noted that the radar signal may be a millimeter wave, a microwave, or an ultrasonic wave. This is not limited in this embodiment of this application.

Optionally, the radar module 110 may be a radar.

Optionally, the radar module 110 may be further configured to sense whether there is a to-be-measured object that meets a measurement condition. When there is the to-be-measured object that meets the measurement condition, distance information of the to-be-measured object is to be measured. The distance information is used to indicate a distance between the to-be-measured object and a transmitting origin of the radar signal.

Optionally, an antenna configuration of the radar may be single-transmit single-receive, or may be a multi-transmit multi-receive antenna array. This is not limited in this embodiment of this application.

The signal processing module 120 is configured to receive the echo signal sent by the radar module, calculate the distance information based on the echo signal, and send the distance information to the output module 130.

The output module 130 is configured to output the distance information.

Optionally, the output module 130 may output the distance information in a plurality of manners. This is not limited in this embodiment of this application.

In a possible implementation, the output module may be a display, and the apparatus 100 may display the distance information by using the display.

In another possible implementation, the output module may be a sound box, and the apparatus 100 may report audio of the distance information by using the sound box.

In still another possible implementation, the output module may be an output interface, and the apparatus 100 may send the distance information to another measurement device by using the output module, so that the another measurement device measures other data based on the distance information.

Optionally, the to-be-measured object is not limited to a person, and may be an animal, a plant, or another object. This is not limited in this embodiment of this application.

Optionally, the distance measurement apparatus is not limited to measuring a height, and may further measure a distance, for example, measure a size or a distance of the to-be-measured object. This is not limited in this embodiment of this application.

Optionally, the apparatus 100 may be an independent distance measurement device, or the apparatus 100 may be integrated into another existing measurement device, and is used as a module that implements a distance measurement function in the measurement device. This is not limited in this embodiment of this application.

Figure 2:
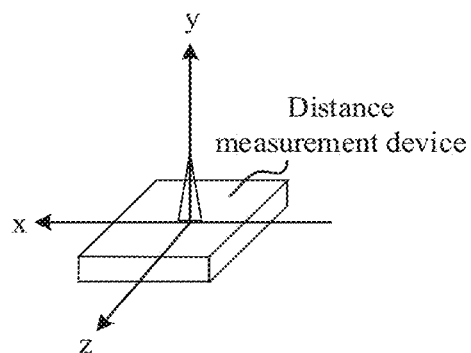
FIG. 2 is a schematic block diagram of a distance measurement device according to an embodiment of this application.

In a possible implementation, FIG. 2 shows a possible product form in which the distance measurement apparatus is an independent distance measurement device (a module inside the distance measurement apparatus is not shown).

Figure 3:
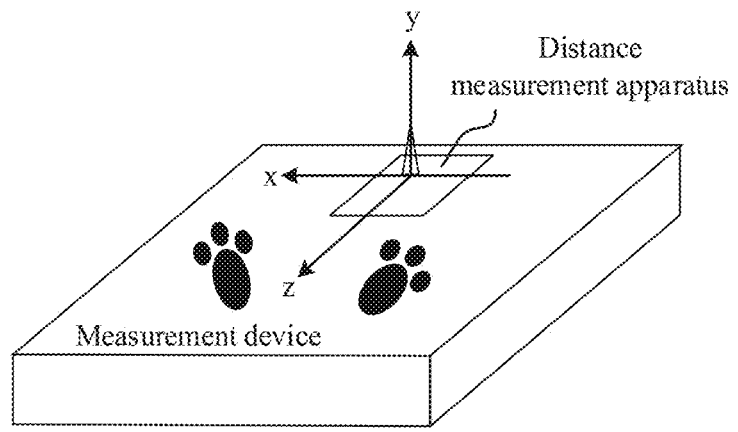
FIG. 3 is a schematic block diagram of a body fat scale according to an embodiment of this application.

In another possible implementation, height measurement is used as an example, and FIG. 3 shows a possible product form in which the distance measurement apparatus is integrated into a measurement device (a module inside the distance measurement apparatus is not shown). A position at which the distance measurement apparatus is disposed does not overlap a position at which a to-be-measured person stands.

For example, the distance measurement apparatus may be integrated into a body fat scale and disposed under a housing of an upper surface of the body fat scale in front of the position at which the to-be-measured person stands.

Optionally, the distance measurement apparatus may alternatively be disposed in another orientation of the position at which the to-be-measured person stands on the body fat scale. This is not limited in this embodiment of this application.

It should be noted that, in FIG. 2 and FIG. 3, a y-axis is a radial direction of the radar signal, an x-axis is a tangential direction of the radar signal, and a z-axis is a vertical direction of the radar signal. A plane including the y-axis and the z-axis is a vertical plane of the radar, and a plane including the x-axis and the y-axis is a horizontal plane of the radar. The distance measured in this embodiment of this application may be understood as a distance of the to-be-measured object in the radial direction.

The foregoing describes, with reference to FIG. 1 to FIG. 3, the distance measurement apparatus provided in this embodiment of this application. The following uses height measurement as an example to describe, with reference to FIG. 4 and FIG. 5, an application scenario provided in this embodiment of this application.

It should be noted that, in this embodiment of this application, only an example in which the to-be-measured object is a person, and a height of the to-be-measured person is measured by using the distance measurement apparatus is used for description. However, this embodiment of this application is not limited thereto.

It should be further noted that, before height measurement is performed, the to-be-measured person needs to first perform measurement preparation.

Figure 4:
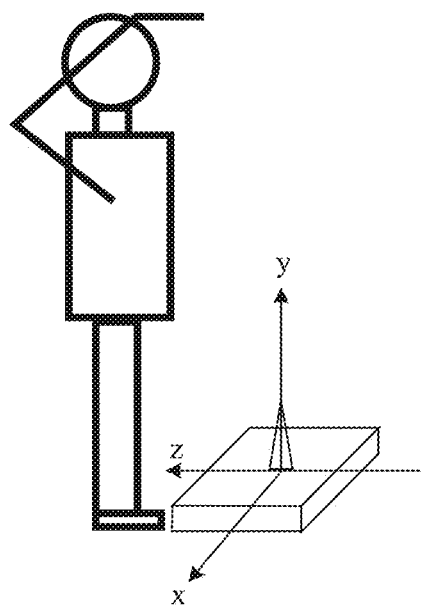
FIG. 4 is a schematic diagram of an application scenario according to an embodiment of this application.

For example, as shown in FIG. 4, when the distance measurement device shown in FIG. 2 is used to measure a height, the distance measurement device is placed on a floor in front of the to-be-measured person. When preparing for measurement, the to-be-measured person extends a palm out of a forehead at a height of a top of a head, enables the palm to be perpendicular to the v-axis of the radar signal, and quickly and slightly shakes the palm, so that slight shaking of the palm at a position of the top of the head can be detected by the radar signal. The distance measurement apparatus determines the height of the to-be-measured person by measuring a distance between the palm and the transmitting origin of the radar signal.

Optionally, the distance measurement device may alternatively be placed in another orientation around a sole of a foot of the to-be-measured person, and the to-be-measured person needs to extend the palm at a corresponding position at the height of the top of the head and slightly shake the palm. This is not limited in this embodiment of this application.

Figure 5:
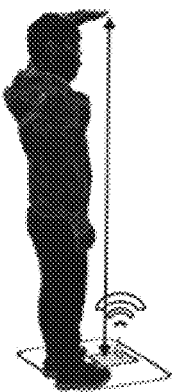
FIG. 5 is a schematic diagram of another application scenario according to an embodiment of this application.

For another example, as shown in FIG. 5, when the measurement device shown in FIG. 3 is used to measure a height, that the measurement device is a body fat scale is used as an example, the to-be-measured person stands on the body fat scale, and the distance measurement apparatus is disposed in front of a sole of a foot of the to-be-measured person. When preparing for measurement, the to-be-measured person extends a palm out of a forehead at a height of a top of a head, enables the palm to be perpendicular to the v-axis of the radar signal, and quickly and slightly shakes the palm, so that slight shaking of the palm at a position of the top of the head can be detected by the radar signal. The distance measurement apparatus determines the height of the to-be-measured person by measuring a distance between the palm and the transmitting origin of the radar signal.

Optionally, the distance measurement apparatus in the body fat scale may alternatively be placed in another orientation around the sole of the foot of the to-be-measured person, and the to-be-measured person needs to extend the palm at a corresponding position at the height of the top of the head and slightly shake the palm. This is not limited in this embodiment of this application.

Optionally, in the application scenario in FIG. 4 or FIG. 5, the to-be-measured person may alternatively use another object (referred to as a target obstacle in this embodiment of this application) to substitute for a hand to shake. This is not limited in this embodiment of this application.

For example, the to-be-measured person extends a ruler or a book out of the head at the height of the top of the head and slightly shakes the ruler or the book.

For another example, a parent or a friend of the to-be-measured person may stand beside the to-be-measured person and extend a hand to substitute for the to-be-measured person to shake at the top of the head of the to-be-measured person.

According to the distance measurement apparatus provided in this embodiment of this application, auxiliary facilities such as a support rod and a support plate are not needed, thereby improving convenience of use. In addition, the radar signal has penetrability, and the distance measurement apparatus may be integrated into another measurement device under a housing of the another measurement device, without affecting product design aesthetics.

In addition, when the radar signal is a microwave radar signal, measurement precision can reach a centimeter level.

Figure 6:
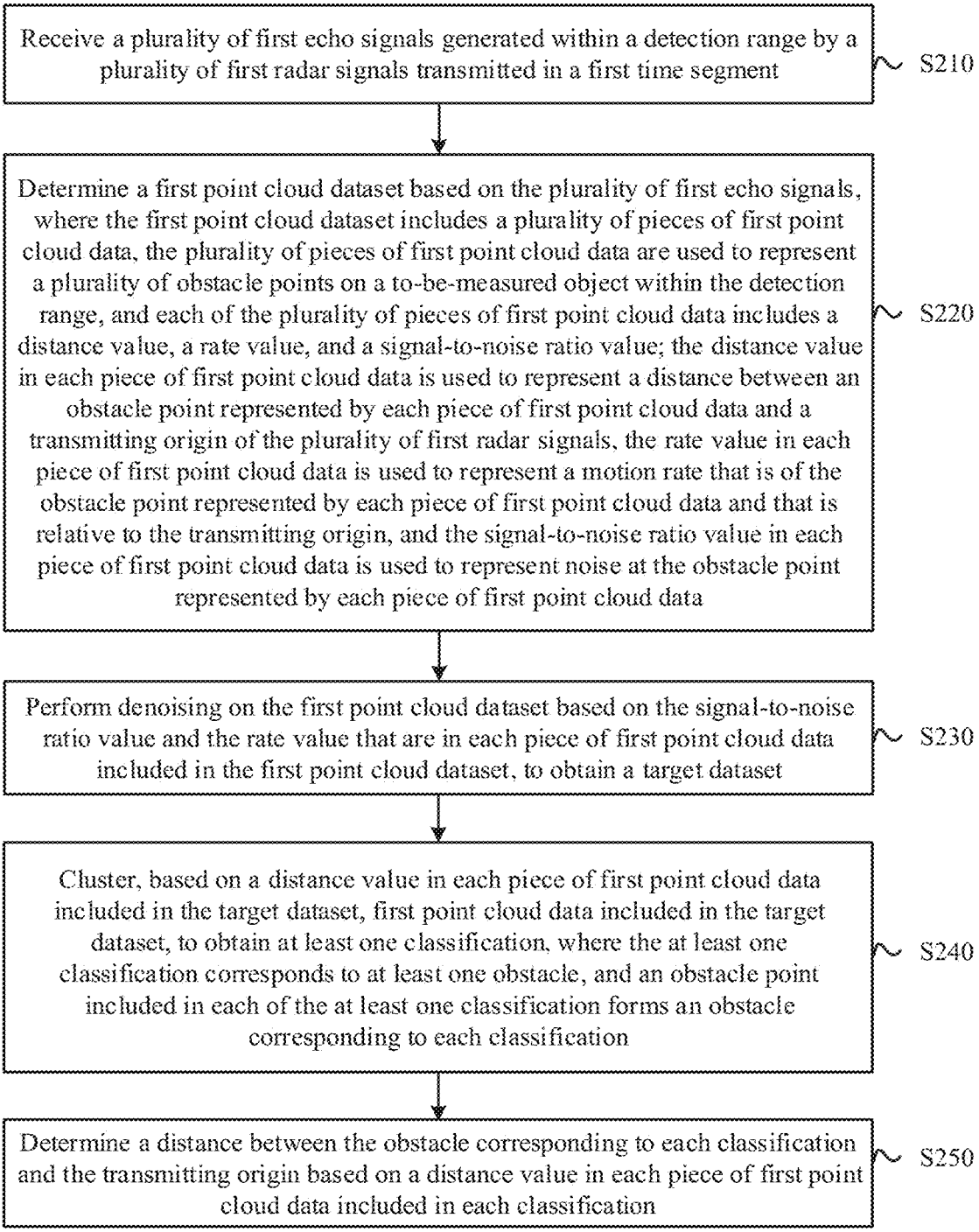
FIG. 6 is a schematic flowchart of a distance measurement method 200 according to an embodiment of this application.

The following describes, with reference to FIG. 6, a schematic flowchart of a distance measurement method 200 provided in an embodiment of this application. The method 200 may be performed by the distance measurement apparatus shown in FIG. 1, and the method 200 is applicable to the application scenario shown in FIG. 4 or FIG. 5.

S210: Receive a plurality of first echo signals generated within a detection range by a plurality of first radar signals transmitted in a first time segment.

It should be noted that, in this embodiment of this application, "first", "second", and the like are only used to distinguish same terms in different time segments, and are irrelevant to a quantity, a type, or the like, unless otherwise specified.

It should be further noted that, in this embodiment of this application, only an example in which a to-be-measured object is a person, and a height of the to-be-measured person is measured by using the distance measurement apparatus is used for description. However, this embodiment of this application is not limited thereto.

It should be noted that, before S210, measurement preparation needs to be first performed on the to-be-measured object, that is, a target obstacle disposed at an end that is of the to-be-measured object and that is farthest from a transmitting origin is slightly shaken.

For example, height measurement is used as an example, and the to-be-measured person needs to extend a hand out of a forehead and slightly shake the hand according to the method described in the application scenario shown in FIG. 4 or FIG. 5.

For example, the distance measurement apparatus periodically transmits K chirp signals within a time of one frame (K=64 to 128), and a frame rate is greater than or equal to 20 Hz, that is, a frame period may be set to 50 to 100 ms. The chirp signal may be expressed as an expression (1):

$$x(t) = A \cos(2\pi f(t)t + \Phi_0) \quad (1)$$

Herein, $$f(t) = \frac{K}{2}t + f_0, K = \frac{B}{t_c},$$

B is bandwidth, $f_0$ is a fixed initial phase, $t_c$ is a chirp signal period, A is an amplitude, and $\Phi_0$ is a start frequency.

Figure 7:
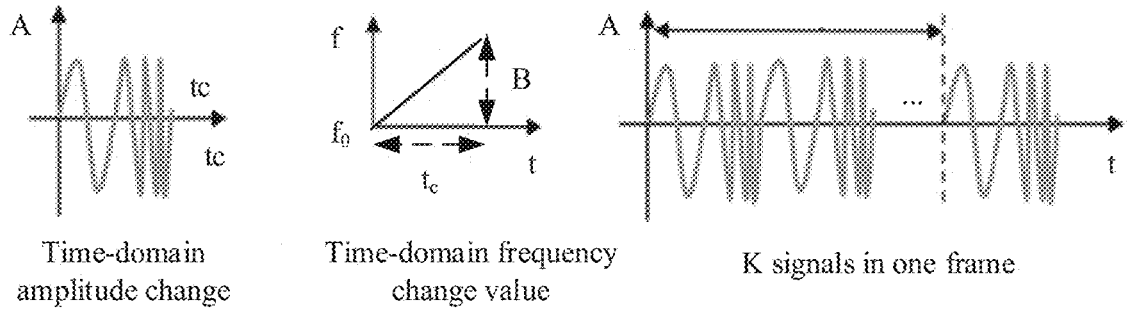
FIG. 7 is a schematic diagram of a radar signal according to an embodiment of this application.

In FIG. 7, a first sub-diagram shows a schematic diagram of a time-domain amplitude change of the chirp signal, a second sub-diagram shows a schematic diagram of a linear frequency change of the chirp signal, and a third sub-diagram shows a schematic diagram of time-domain amplitude changes of K chirp signals within a time of one frame.

It should be noted that, in this embodiment of this application, bandwidth of the first radar signal transmitted by the distance measurement apparatus is greater than 3 GHz, a quantity of transmit antennas in the distance measurement apparatus is greater than or equal to 1, a quantity of receive antennas is greater than or equal to 1, and a 3 dB beam width of antenna radiation needs to be less than or equal to 90° on both a horizontal plane (H-plane) and a vertical plane (E-plane), that is, main lobe beams need to be concentrated.

Optionally, in this embodiment of this application, only an example in which the first radar signal is the chirp signal is used for description, and the distance measurement apparatus may alternatively transmit another type of radar signal. This is not limited in this embodiment of this application.

S220: Determine a first point cloud dataset based on the plurality of first echo signals, where the first point cloud dataset includes a plurality of pieces of first point cloud data, the plurality of pieces of first point cloud data are used to represent a plurality of obstacle points on a to-be-measured object within the detection range, and each of the plurality of pieces of first point cloud data includes a distance value, a rate value, and a signal-to-noise ratio value; the distance value in each piece of first point cloud data is used to represent a distance between an obstacle point represented by each piece of first point cloud data and a transmitting origin of the plurality of first radar signals, the rate value in each piece of first point cloud data is used to represent a motion rate that is of the obstacle point represented by each piece of first point cloud data and that is relative to the transmitting origin, and the signal-to-noise ratio value in each piece of first point cloud data is used to represent noise at the obstacle point represented by each piece of first point cloud data.

In a possible implementation, a plurality of first spectrum data groups corresponding to the plurality of first echo signals may be determined based on the plurality of first echo signals, where each of the plurality of first spectrum data groups includes a plurality of pieces of first spectrum data, the plurality of pieces of first spectrum data represent the plurality of obstacle points within the detection range, and each of the plurality of pieces of first spectrum data includes a distance value and a signal strength value; the distance value in each piece of first spectrum data is used to represent a distance between an obstacle point represented by each piece of first spectrum data and the transmitting origin, the signal strength value in each piece of first spectrum data is used to represent reflection strength that is of a first radar signal corresponding to each piece of first spectrum data and that is at the obstacle point represented by each piece of first spectrum data, and a plurality of distance values included in each first spectrum data group are the same. The first point cloud dataset is determined based on the distance value and the signal strength value that are in each piece of first spectrum data.

For example, it is assumed that r(n) is a baseband discrete sampled signal obtained after demodulation of a single chirp signal received by the receive antenna, and n is a quantity of samples within a single chirp signal period. $N_1$-point fast Fourier transformation (FFT) calculation, that is, 1-dimensional (1D)-FFT calculation, is performed on r(n) by using the following expression (2), to obtain a Range-FFT (also referred to as a distance spectrum) R(k).

$$R(k) = FT(r(n), N_1), N_1 \geq n_1 \quad (2)$$

Figure 8:
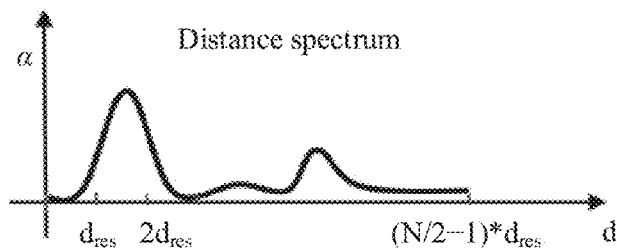
FIG. 8 is a schematic diagram of a Range-FFT according to an embodiment of this application.

It should be noted that FIG. 8 shows the Range-FFT. The Range-FFT is defined as a vector including modulus values $$\alpha_i \left( i = 0, 1, \ldots, \frac{N_1}{2} - 1 \right)$$

of $N_1/2$ complex numbers of R(k) in a positive frequency domain, each value corresponds to one frequency (range-bin), and a range-bin range is $$\left( 0 \sim \frac{N_1}{2} - 1 \right),$$

where $$d_{res} = \frac{C}{2B} * \frac{n}{N_1}$$

is a distance corresponding to a single range-bin, that is, distance resolution. A maximum detection distance is $$d_{max} = d_{res} * \left( \frac{N_1}{2} - 1 \right).$$

As shown in FIG. 8, the Range-FFT includes $N_1/2$ frequencies, a horizontal axis value corresponding to each frequency represents a distance between an obstacle point represented by the frequency and the transmitting origin of the first radar signal, and a vertical axis value corresponding to each frequency represents reflection strength that is of the first radar signal and that is at the obstacle point represented by the frequency. One obstacle within the detection range of the first radar signal may include at least one obstacle point.

That is, K R(k) sequences, that is, K Range-FFTs, may be obtained from the K chirp signals, where one Range-FFT is referred to as one first spectrum data group. A distance value and a reflection strength value that are corresponding to one frequency in the Range-FFT are referred to as one piece of first spectrum data in the first spectrum data group.

Figure 9:
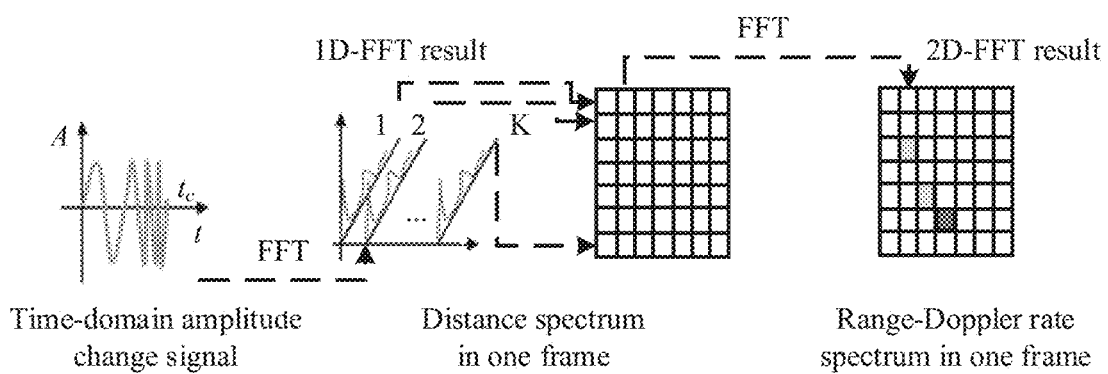
FIG. 9 is a schematic diagram of a 2D-FFT processing process of a radar signal according to an embodiment of this application.

For example, a first sub-diagram to a second sub-diagram in FIG. 9 show a process of performing 1D-FFT calculation on a single chirp signal to obtain a Range-FFT. The second sub-diagram to a third sub-diagram show a complex matrix including $$K * \frac{N_1}{2}$$

complex numbers obtained by arranging the K Range-FFTs in rows, and each complex number (that is, one square in the third sub-diagram in FIG. 9) in the complex matrix includes a real part and an imaginary part. The real part represents a range-bin, and the imaginary part represents signal reflection strength at the range-bin.

Then, FFT calculation of a second dimension, that is, 2-dimensional (2D)-FFT calculation, is performed on a sequence including K values at a same range-bin in each of the K R(k) sequences, to obtain a Range-Doppler (also referred to as a range-Doppler rate spectrum).

In a possible implementation, the third sub-diagram to a fourth sub-diagram in FIG. 9 show a process of further performing $N_2$-point FFT calculation, that is, 2D-FFT calculation, on each column of the K Range-FFTs, to obtain a Range-Doppler. The Range-Doppler is expressed as a complex matrix including $$\frac{N_2}{2} * \frac{N_1}{2}$$

complex numbers, and each complex number (that is, one square in the fourth sub-diagram in FIG. 9) in the complex matrix includes a real part and an imaginary part. The real part represents a range-bin, and the imaginary part represents a Doppler rate value. Each square of Doppler-bin corresponds to rate resolution $v_{res}$, and a rate value range of the Range-Doppler is $$-\frac{N_2}{2} * v_{res} \text{ to } \left(\frac{N_2}{2} - 1\right) * v_{res}.$$

As shown in the fourth sub-diagram in FIG. 9, one square in the Range-Doppler is one complex number in the complex matrix, and a complex number at each square corresponds to an obstacle point. A real part of the complex number represents a distance value between the obstacle point and the transmitting origin of the first radar signal, and an imaginary part represents a Doppler rate value that is of the obstacle point and that is relative to the transmitting origin. A color of the square represents a signal-to-noise value at the obstacle point, that is, an SNR value. A darker color indicates a larger SNR value.

It should be noted that information of three dimensions, that is, the real part and the imaginary part of the complex number at each square in the Range-Doppler and the color of each square, is referred to as one piece of first point cloud data. First point cloud data corresponding to all squares in K Range-Doppler rate spectra forms a first point cloud dataset.

That is, the plurality of pieces of first point cloud data represent a plurality of obstacle points on the to-be-measured object within the detection range, and each of the plurality of pieces of first point cloud data includes a distance value, a rate value, and a signal-to-noise ratio value. The distance value in each piece of first point cloud data is used to represent a distance between an obstacle point represented by each piece of first point cloud data and the transmitting origin, the rate value in each piece of first point cloud data is used to represent a motion rate that is of the obstacle point and that is relative to the transmitting origin, and the signal-to-noise ratio value in each piece of first point cloud data is used to represent noise at the obstacle point.

Optionally, the first point cloud data in this embodiment of this application may be represented in a plurality of formats. This is not limited in this embodiment of this application.

In a possible implementation, the first point cloud data may be represented by using a format 1 in the following expression (3):

$$\alpha = [r, v, s] \tag{3}$$

Herein, r is a distance value, v is a modulus value of a Doppler rate, and s is an SNR value.

In another possible implementation, when a radar of the distance measurement apparatus has a multiple-input multiple-output (MIMO) antenna array, for example, a 3×4 MIMO antenna array of three transmit antennas and four receive antennas, the radar may estimate an angle of the first echo signal, and may estimate, based on an estimated horizontal azimuth, horizontal two-dimensional coordinates of a data point corresponding to each square in the Range-Doppler. Therefore, the first point cloud data may be represented by using a format 2 in the following expression (4):

$$\alpha = [x, y, v, s] \tag{4}$$

Herein, a y-axis is a horizontal radial direction of the radar, an x-axis is a horizontal tangential direction of the radar, v is a modulus value of a Doppler rate, and s is an SNR value.

In still another possible implementation, when a radar of the distance measurement apparatus has a MIMO antenna array, the radar may estimate an angle of the first echo signal, may estimate, based on an estimated horizontal azimuth, horizontal two-dimensional coordinates of a data point corresponding to each square in the Range-Doppler, and may estimate, based on an estimated vertical azimuth, three-dimensional coordinates of a data point corresponding to each square. Therefore, the first point cloud data may be represented by using a format 3 in the following expression (5):

$$\alpha = [x, y, z, v, s] \tag{5}$$

Herein, a v-axis is a horizontal radial direction of the first radar signal, an x-axis is a horizontal tangential direction of the first radar signal, a z-axis is a vertical direction of the first radar signal, v is a modulus value of a Doppler rate, and s is an SNR value.

That is, the distance value in each piece of first point cloud data includes a distance component value in the radial direction and a distance component value in the tangential direction of the first radar signal that are of the obstacle point represented by each piece of first point cloud data; or the distance value in each piece of first point cloud data includes the distance component value in the radial direction, the distance component value in the tangential direction, and a distance component value in the vertical direction of the first radar signal that are of the obstacle point represented by each piece of first point cloud data.

Therefore, the first point cloud dataset $\varphi$ in the K Range-Doppler rate spectra may be represented by using the following expression (6):

$$\varphi = [\alpha_0, \alpha_1, \ldots, \alpha_{n-1}] \tag{6}$$

Herein, $\alpha_i$ represents one piece of first point cloud data.

S230: Perform denoising on the first point cloud dataset based on the signal-to-noise ratio value and the rate value that are in each piece of first point cloud data included in the first point cloud dataset, to obtain a target dataset.

It should be noted that, because rates at obstacle points in different motion statuses are different, a rate at an obstacle point that forms the target obstacle shaking at the top of a head of the to-be-measured person is different from a rate at another surrounding obstacle point.

Optionally, denoising is performed on the first point cloud dataset based on the signal-to-noise ratio value and the rate value that are in each piece of first point cloud data included in the first point cloud dataset, a preset signal-to-noise ratio threshold, and a preset rate threshold, to obtain the target dataset, where the rate threshold is determined based on a rate of the target obstacle in at least one obstacle.

In a possible implementation, the rate of the target obstacle may be equal to the rate threshold.

In another possible implementation, the rate of the target obstacle may be slightly greater than the rate threshold.

It should be noted that a reflector with rate information is extracted to the first point cloud data in the distance measurement method in this embodiment of this application, and when rate resolution of the radar reaches 0.08 m/s, the radar can identify an obstacle with a slight vibration, for example, a slight vibration of a trunk when a body is in a static state. First point cloud data formed by such a vibrating object interferes with distance measurement of the target obstacle and needs to be filtered out. Therefore, interference may be filtered out by using the rate threshold.

In addition, in the distance measurement method in this embodiment of this application, slight shaking of the target obstacle is detected. Strength of an echo signal generated by such slight shaking is relatively weak, and a signal-to-noise ratio is not high. Therefore, noise may be filtered out by using the signal-to-noise ratio threshold.

In conclusion, first point cloud data whose $v \leq v_{th}$ and $s \geq s_{th}$ in the first point cloud dataset may be filtered out, to reduce interference and noise, where $v_{th}$ is a preset rate threshold, and $s_{th}$ is a preset noise threshold.

For example, a value of $v_{th}$ may be set to 0.16 m/s, and $s_{th}$ and $v_{th}$ may be set based on a motion rate of the target obstacle. In addition, $s_{th}$ may be set to different values depending on different platforms.

The target first point cloud dataset P' obtained after denoising may be represented by using the following expression (7):

$$\varphi' = [\alpha'_0, \alpha'_1, \ldots, \alpha'_{n-1}] s.t. v_i \geq v_{th} \& s_i \leq s_{th} \qquad (7)$$

Optionally, in a denoising process in this embodiment of this application, denoising may alternatively be performed only based on the rate threshold. This is not limited in this embodiment of this application.

S240: Cluster, based on a distance value in each piece of first point cloud data included in the target dataset, first point cloud data included in the target dataset, to obtain at least one classification, where the at least one classification corresponds to at least one obstacle, and an obstacle point included in each of the at least one classification forms an obstacle corresponding to each classification.

It should be noted that the at least one obstacle obtained through clustering includes the target obstacle, the target obstacle includes a first obstacle point and a second obstacle point, and a distance between the first obstacle point and the second obstacle point is less than a preset distance threshold.

That is, a characteristic quantity of each piece of first point cloud data is extracted from the target first point cloud dataset P' for clustering.

Optionally, in this embodiment of this application, a plurality of clustering methods may be used to cluster the first point cloud data in the target first point cloud dataset. This is not limited in this embodiment of this application.

In a possible implementation, the first point cloud data in the target first point cloud dataset may be clustered by using density-based spatial clustering of applications with noise (DBSCAN).

Optionally, first point cloud data in different formats may be clustered based on different information. This is not limited in this embodiment of this application.

In a possible implementation, the first point cloud data included in the target dataset may be clustered based on the distance value in each piece of first point cloud data included in the target dataset, to obtain the at least one classification.

That is, for the format 1 that is of the first point cloud data and that is shown in the expression (3), [r, v] may be extracted as a single piece of first point cloud data for clustering.

In another possible implementation, the first point cloud data included in the target dataset may be clustered based on the distance value and a rate value that are in each piece of first point cloud data included in the target dataset, to obtain the at least one classification.

That is, for the format 2 that is of the first point cloud data and that is shown in the expression (4) and the format 3 that is of the first point cloud data and that is shown in the expression (5), [x, y] or [x, y, v] may be extracted as a single piece of first point cloud data for clustering.

S250: Determine a distance between the obstacle corresponding to each classification and the transmitting origin based on a distance value in each piece of first point cloud data included in each classification.

It should be noted that the at least one classification includes a target classification corresponding to the target obstacle. Height measurement is used as an example, the target obstacle is disposed at the top of a head of a to-be-measured person, and the distance between the target obstacle and the transmitting origin may be understood as a height of the to-be-measured person.

Optionally, the target classification may be determined from the at least one classification, and an obstacle point represented by each piece of first point cloud data included in the target classification forms the target obstacle.

In a possible implementation, a classification that includes a largest amount of first point cloud data in the at least one classification may be determined as the target classification.

Optionally, the first point cloud data included in the target classification may be represented by using the following expression (8):

$$\varphi'' = [\alpha''_0, \alpha''_1, \ldots, \alpha''_{m-1}] \qquad (8)$$

Figure 10:
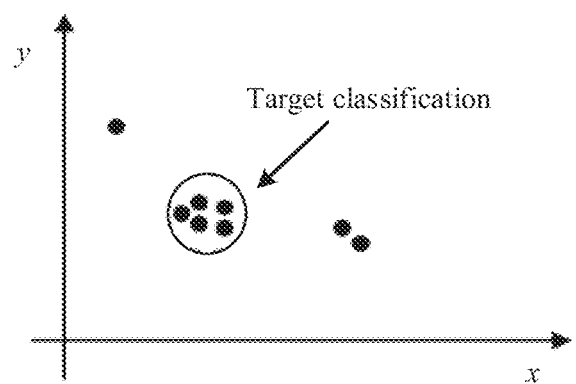
FIG. 10 is a schematic diagram of a clustering process according to an embodiment of this application.

For example, a DBSCAN algorithm is used as an example, and when a value of a key parameter ε-neighborhood of the algorithm is 0.8, and a value of a minimum quantity MinPts of core object sample points is 5, selection of the target classification may be shown by a dashed circle in FIG. 10.

According to the distance measurement method in this embodiment of this application, clustering the first point cloud data in the target first point cloud dataset and selecting the target classification help further eliminate interference caused by an outlier. The outlier comes from environmental interference other than the target obstacle, and also comes from an estimation error of a signal parameter generated by shaking of the target obstacle, such as deviations of coordinates x and y caused by an angle estimation error, and these parameters are to be used for distance measurement in a next step. Therefore, interference from an interfering point can be further reduced through clustering, thereby improving accuracy of distance measurement.

Optionally, height measurement is used as an example, and based on different formats of the first point cloud data included in the target classification, different methods may be used to determine a height value of the to-be-measured person, that is, a distance between a target obstacle at the top of the head of the to-be-measured person and the transmitting origin.

In a possible implementation, when the first point cloud data included in the target classification uses the format 1 that is of the first point cloud data and that is shown in the expression (3), a current instantaneous height value h may be represented by using an expression (9):

$$h = \Sigma_{i=0}^{m-1} w_i \times r^*_i \quad (9)$$

Herein, $w_i$ is a weighting factor, $\Sigma_{i=0}^{m-1} w_i = 1$, and $r_i$ is a distance value in an $i^{th}$ piece of first point cloud data in the target classification.

In another possible implementation, when the first point cloud data included in the target classification uses the format 2 that is of the first point cloud data and that is shown in the expression (4) and the format 3 that is of the first point cloud data and that is shown in the expression (5), a current instantaneous height value h may be represented by using an expression (10):

$$h = \Sigma_{i=0}^{m-1} w_i \times r^*_i \quad (10)$$

Herein, $w_i$ is a weighting factor, $\Sigma_{i=0}^{m-1} w_i = 1$, and $y_i$ is a y-axis component of a distance value in an $i^{th}$ piece of first point cloud data in the target classification.

It should be noted that the current instantaneous height value in this embodiment of this application is a height value measured based on K chirp signals in one current frame.

Optionally, $w_i$ in this embodiment of this application may be determined in a plurality of manners. This is not limited in this embodiment of this application.

In a possible implementation, values of $w_i$ are equal, that is, $w_i = 1/m$.

In another possible implementation, a value of $w_i$ is related to a signal-to-noise ratio, for example, $$w_i = \frac{s''_i}{\sum_{k=0}^{m-1} s''_i},$$

where $s''_i$ is a signal-to-noise ratio value in an $i^{th}$ piece of first point cloud data in the target classification.

According to the distance measurement method provided in this embodiment of this application, a y-axis component of a distance value in the first point cloud data reflects a real distance in the radial direction of the radar. Therefore, accuracy of distance measurement can be improved by weighting a y-axis component of a distance value in each piece of first point cloud data in the target classification.

In addition, according to the distance measurement method provided in this embodiment of this application, interference noise caused by a surrounding obstacle, a slight vibration of a trunk of a human body, or the like can be effectively eliminated, thereby effectively improving measurement accuracy. In addition, the distance measurement method can adapt to a more complex measurement environment.

In addition, when height measurement is performed, a requirement of an adult to measure a height of a nearby child can be met, thereby improving practicability.

It should be noted that height measurement is used as an example, and an instantaneous height value obtained by performing S210 to S250 is affected by noise interference, hand lifting, hand falling, a slight trunk vibration, and the like, causing a large change in the instantaneous value. Therefore, accuracy and stability of a measured height value may be improved by using the following two methods.

Method 1:

Statistics on a variance $\sigma_h^2$ of an instantaneous height value measured at each of consecutive frame time points within 1s are collected. If $\sigma_h^2 \leq \sigma_{th1}$, an average value of instantaneous height values measured at all frames within 1s is used as a final height value of a to-be-measured person. $\sigma_{th1}$ is a preset first variance threshold, and a value range of the first variance threshold is a first threshold range.

Figure 11:
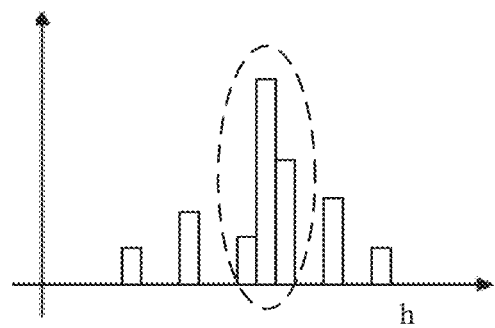
FIG. 11 is a histogram of a distance value according to an embodiment of this application.

Method 2:

Statistics on a variance $\sigma_h^2$ of an instantaneous height value obtained at each of consecutive frame time points in a plurality of seconds are collected. If $\sigma_h^2 \leq \sigma_{th2}$, a height value interval with most concentrated distribution, for example, an interval in a dashed circle in FIG. 11, is extracted by using histogram distribution, and then an average value of height values included in the interval is used as a final height value of a to-be-measured person. $\sigma_{th2}$ is a preset second variance threshold, and a value range of the second variance threshold is a second threshold range. The second threshold range is greater than the first threshold range.

According to the method 1 and the method 2, an invalid measurement value under interference such as large-amplitude shaking of a human body can be eliminated, so that measurement accuracy and measurement stability are improved.

It should be noted that, before determining the first point cloud dataset based on the distance value and the signal strength value that are in each piece of first spectrum data, the distance measurement apparatus may first determine whether a position of the to-be-measured object meets a measurement condition, and then perform distance measurement when the position of the to-be-measured object meets the measurement condition. When the position of the to-be-measured object does not meet the measurement condition, a distance measurement function may be suspended, to reduce energy consumption.

In a possible implementation, whether the position of the to-be-measured object meets the measurement condition may be determined in the following manner: receiving a plurality of second echo signals generated within the detection range by a plurality of second radar signals transmitted in a second time segment, where an end time point of the second time segment is not later than an end time point of the first time segment; determining, based on the plurality of second echo signals, a plurality of second spectrum data groups corresponding to the plurality of second echo signals, where each of the plurality of second spectrum data groups includes a plurality of pieces of second spectrum data, the plurality of pieces of second spectrum data represent the plurality of obstacle points within the detection range, and each of the plurality of pieces of second spectrum data includes a distance value and a signal strength value; the distance value in each piece of second spectrum data is used to represent a distance between an obstacle point represented by each piece of second spectrum data and the transmitting origin, the signal strength value in each piece of second spectrum data is used to represent reflection strength that is of a second radar signal corresponding to each piece of second spectrum data and that is at the obstacle point represented by each piece of second spectrum data, and a plurality of distance values included in each second spectrum data group are the same; and determining, based on the distance value and the signal strength value that are in each piece of second spectrum data, whether the position of the to-be-measured object meets the measurement condition.

Optionally, that the end time point of the second time segment is not later than the end time point of the first time segment may include: The end time point of the second time segment is earlier than the end time point of the first time segment; or the end time point of the second time segment is equal to the end time point of the first time segment. This is not limited in this embodiment of this application.

Optionally, duration of the second time segment may be the same as or different from duration of the first time segment. This is not limited in this embodiment of this application.

In a possible implementation, a process of determining whether the position of the to-be-measured object meets the measurement condition may be performed before the first point cloud dataset is determined. That is, Range-FFTs obtained based on echo signals of chirp signals transmitted in a plurality of time segments may be cached in a cache of the distance measurement apparatus, and a Range-FFT of each chirp signal is stored in and deleted from the cache based on a first in first out rule. When that the position of the to-be-measured object meets the measurement condition is determined based on Range-FFTs obtained from echo signals (that is, second echo signals) of a plurality of chirp signals (that is, second radar signals) in the second time segment, the first point cloud dataset continues to be determined based on the plurality of first echo signals in the first time segment, and distance measurement is performed.

Optionally, in this embodiment of this application, whether the position of the to-be-measured object meets the measurement condition may be determined in a plurality of manners based on the distance value and the signal strength value that are in each piece of second spectrum data. This is not limited in this embodiment of this application.

In a possible implementation, normalization processing may be performed on a signal strength value corresponding to each of the plurality of distance values included in each second spectrum data group, to obtain a normalized signal strength value corresponding to each of the plurality of distance values included in each second spectrum data group; a variance value of a signal strength value corresponding to each of the plurality of distance values is determined based on a normalized signal strength value corresponding to a same distance value in the plurality of second spectrum data groups; and whether the position of the to-be-measured object meets the measurement condition is determined based on the variance value of the signal strength value corresponding to each of the plurality of distance values.

It should be noted that, for a process of determining, based on the plurality of second echo signals, the plurality of second spectrum data groups corresponding to the plurality of second echo signals, that is, obtaining P Range-FFTs based on P chirp signals transmitted in the second time segment, refer to the foregoing processing of the plurality of first echo signals. To avoid repetition, details are not described herein.

Figure 12:
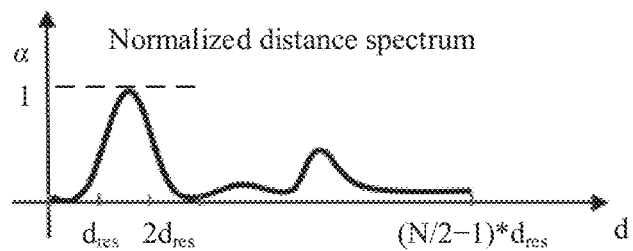
FIG. 12 is a schematic diagram of a normalized Range-FFT according to an embodiment of this application.

In a possible implementation, a process of performing normalization processing on each of the P Range-FFTs includes: Step 1: Search for a maximum amplitude $\alpha_{max}=(\alpha_i)$, i=0, 1, . . . , $$\frac{N_1}{2}-1$$

in the Range-FFT. Step 2: Divide an amplitude at each range-bin in the Range-FFT by the maximum amplitude, to obtain a normalized Range-FFT $$\alpha'_i = \frac{\alpha_i}{\alpha_{max}}, i = 0, 1, \ldots, \frac{N_1}{2}-1$$

at a current frame time point, as shown in FIG. 12.

Then, a variance of an amplitude at each range-bin in P normalized Range-FFTs is calculated, to obtain a variance value of a normalized amplitude corresponding to each range-bin.

Figure 13:
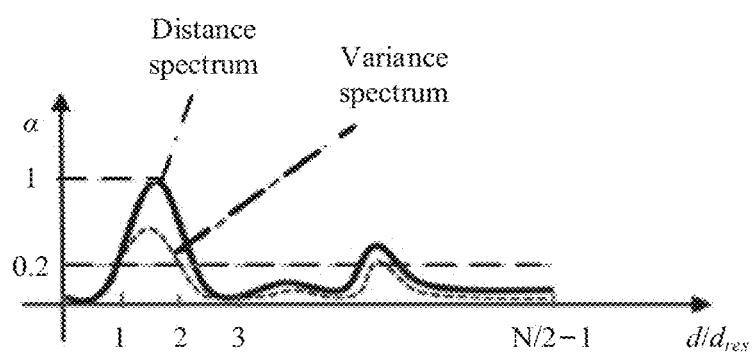
FIG. 13 is a schematic diagram of a variance value of a normalized Range-FFT according to an embodiment of this application.

In a possible implementation, the P normalized Range-FFTs in the second time segment may be expressed as $\varphi_i=[\alpha_i^0, \alpha_i^1, \ldots, \alpha_i^P]^T$, where P is a quantity of chirp signals in the second time segment, and $$\alpha_t^i = \left[\alpha_i^0, \alpha_i^1, \ldots, \alpha_i^{\frac{N_1}{2}-1}\right]$$

is a normalized Range-FFT of an $i^{th}$ chirp signal. Therefore, $\varphi_i$ is a $$P \times \frac{N_1}{2}$$

matrix. A variance of an element in each column of $\varphi_i$ is calculated, that is, a variance $(\varphi_i^m)^2$ of a value at each range-bin is calculated, to obtain a variance curve spectrum $$\sigma_t = \left[\sigma_t^0, \sigma_t^1, \ldots, \sigma_t^{\frac{N_1}{2}-1}\right],$$

where $\varphi_i^"$ is a standard deviation at an $m^{th}$ range-bin, as shown by a dashed line in FIG. 13.

Optionally, in this embodiment of this application, whether the position of the to-be-measured object meets the measurement condition may be determined in a plurality of manners based on the variance value of the signal strength value corresponding to each of the plurality of distance values, that is, the variance value of the normalized amplitude corresponding to each range-bin. This is not limited in this embodiment of this application.

In a possible implementation, when a quantity of variance values that are greater than a third variance threshold (as shown in FIG. 13, the third variance threshold is 0.2) and that are of signal strength values corresponding to all of the plurality of distance values is greater than or equal to a quantity threshold, it is determined that the position of the to-be-measured object meets the measurement condition; or when the quantity of variance values that are greater than the third variance threshold and that are of signal strength values corresponding to all of the plurality of distance values is less than the quantity threshold, it is determined that the position of the to-be-measured object does not meet the measurement condition.

For example, height measurement is used as an example. When the quantity of variance values that are greater than the third variance threshold and that are of signal strength values corresponding to all of the plurality of distance values is $k>k_{th}$, it is determined that a position of a to-be-measured person meets the measurement condition, that is, the to-be-measured person is close to the apparatus, and effective measurement may be started. In addition, the to-be-measured person is prompted to prepare for measurement, and the to-be-measured person may complete measurement preparation according to the actions described in the application scenarios in FIG. 4 and FIG. 5. When the quantity of variance values that are greater than the third variance threshold and that are of signal strength values corresponding to all of the plurality of distance values is $k \leq k_{th}$, it is determined that the position of the to-be-measured person does not meet the measurement condition, that is, the to-be-measured person is far away from the apparatus, and the to-be-measured person may be reminded to approach. When the quantity of variance values that are greater than the third variance threshold and that are of signal strength values corresponding to all of the plurality of distance values is $k=0$, it is determined that there is no person in a current detection area, and distance measurement may be stopped, or a sleep mode may be entered. Herein, $k_{th}$ is the quantity threshold.

According to the distance measurement apparatus provided in this embodiment of this application, it is not necessary to use an external sensor such as a human body infrared sensor or a pressure sensor to determine whether the distance measurement function may be started, thereby simplifying the measurement apparatus, and reducing power consumption and costs.

Figure 14:
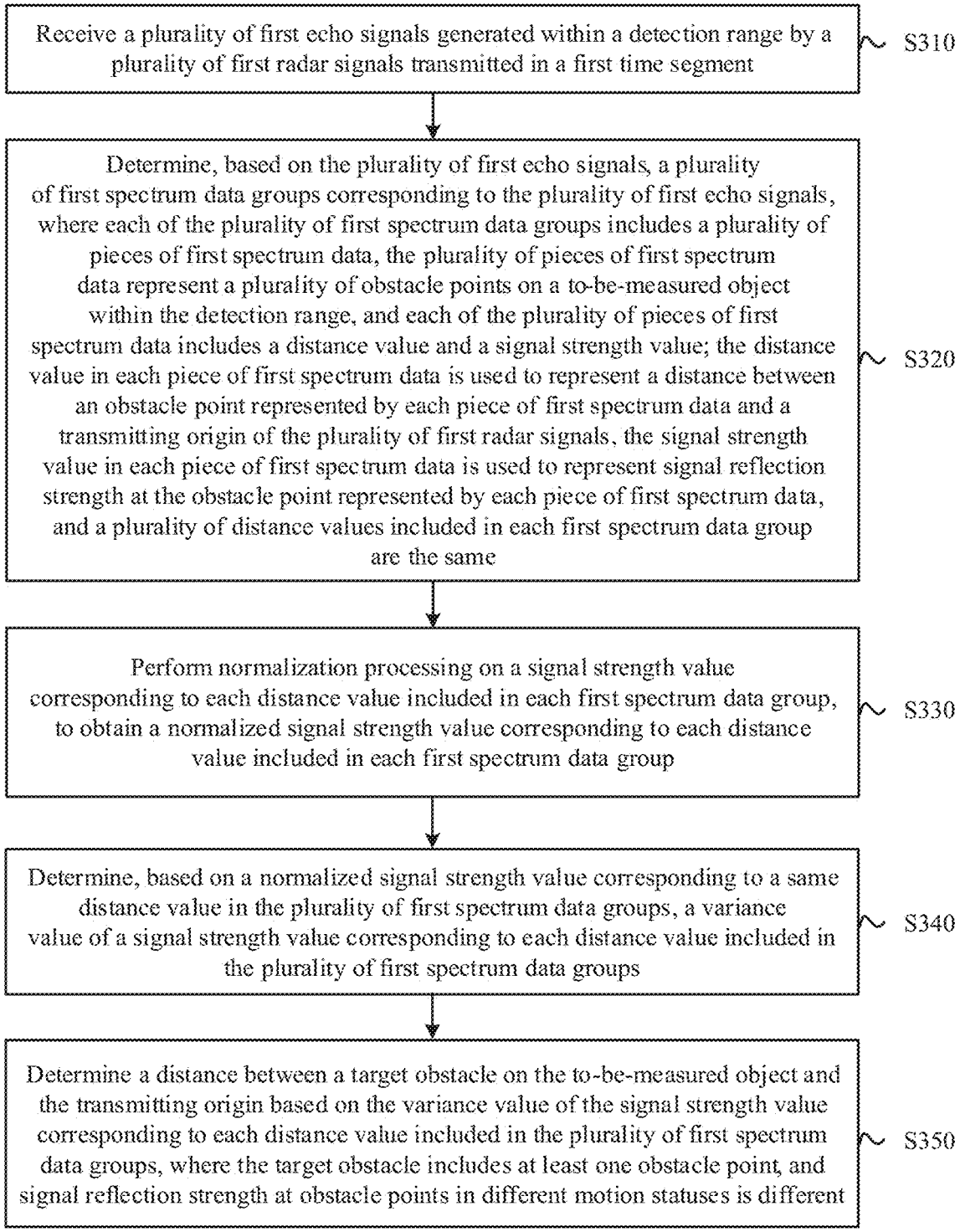
FIG. 14 is a schematic flowchart of a distance measurement method 300 according to an embodiment of this application.

FIG. 14 shows a schematic flowchart of a distance measurement method 300 according to an embodiment of this application. The method 300 may be performed by the distance measurement apparatus shown in FIG. 1.

S310: Receive a plurality of first echo signals generated within a detection range by a plurality of first radar signals transmitted in a first time segment.

S320: Determine, based on the plurality of first echo signals, a plurality of first spectrum data groups corresponding to the plurality of first echo signals, where each of the plurality of first spectrum data groups includes a plurality of pieces of first spectrum data, the plurality of pieces of first spectrum data represent a plurality of obstacle points on a to-be-measured object within the detection range, and each of the plurality of pieces of first spectrum data includes a distance value and a signal strength value; the distance value in each piece of first spectrum data is used to represent a distance between an obstacle point represented by each piece of first spectrum data and a transmitting origin of the plurality of first radar signals, the signal strength value in each piece of first spectrum data is used to represent signal reflection strength at the obstacle point represented by each piece of first spectrum data, and a plurality of distance values included in each first spectrum data group are the same.

S330: Perform normalization processing on a signal strength value corresponding to each distance value included in each first spectrum data group, to obtain a normalized signal strength value corresponding to each distance value included in each first spectrum data group.

S340: Determine, based on a normalized signal strength value corresponding to a same distance value in the plurality of first spectrum data groups, a variance value of a signal strength value corresponding to each distance value included in the plurality of first spectrum data groups.

It should be noted that, for an implementation process of S310 to S340, refer to corresponding descriptions in the method 200. To avoid repetition, details are not described herein.

S350: Determine a distance between a target obstacle on the to-be-measured object and the transmitting origin based on the variance value of the signal strength value corresponding to each distance value included in the plurality of first spectrum data groups, where the target obstacle includes at least one obstacle point, and signal reflection strength at obstacle points in different motion statuses is different.

It should be noted that height measurement is used as an example, the target obstacle is disposed at the top of a head of a to-be-measured person, and the distance between the target obstacle and the transmitting origin may be understood as a height of the to-be-measured person.

In a possible implementation, the distance between the target obstacle and the transmitting origin may be determined based on the variance value of the signal strength value corresponding to each distance value included in the plurality of first spectrum data groups and a first variance threshold, where the first variance threshold is determined based on signal strength at the at least one obstacle point that forms the target obstacle.

Figure 15:
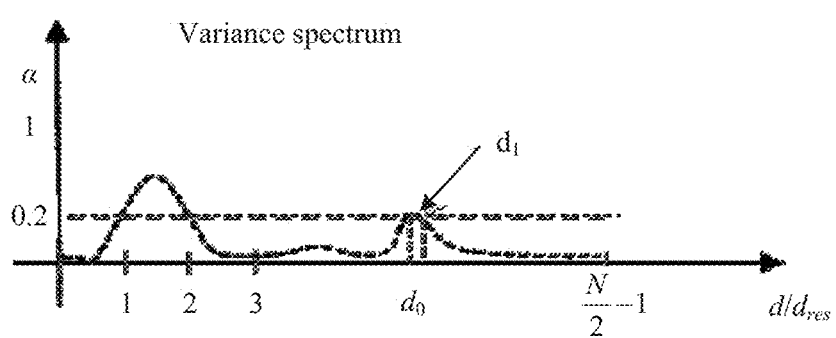
FIG. 15 is a schematic diagram of a variance value of another normalized Range-FFT according to an embodiment of this application.

It should be noted that height measurement is used as an example, and during measurement preparation, a user extends a palm and slightly shakes the palm at the top of a head, so that a variance value at a range-bin corresponding to a height of the top of the head is increased. Therefore, a distance value, for example, do in FIG. 15, corresponding to a farthest wave peak that is in a Range-FFT variance curve spectrum and whose value is greater than or equal to a variance threshold is searched for within a distance threshold range and is used as a current instantaneous height value; or a largest distance value, for example, $d_1$ in FIG. 15, whose variance is greater than or equal to the variance threshold is used as the current instantaneous height value.

It should be noted that the distance threshold may be considered to be set to a value that is greater than the height of the to-be-measured person and less than or equal to a height of a ceiling, for example, 2.5 m, and the variance threshold may be set to a variance value that can be caused, for example, 0.2, so that a height at which the palm is shaken is included.

It should be further noted that the method 300 may also use the method for improving accuracy of distance measurement described in the method 200 and the method for determining whether there is a to-be-measured object that meets a measurement condition described in the method 200. To avoid repetition, details are not described herein.

FIG. 16 shows a schematic flowchart of a distance measurement method 400 according to an embodiment of this application. The method 400 may be performed by the distance measurement apparatus shown in FIG. 1.

S410: Receive a plurality of first echo signals generated within a first detection range by a plurality of first radar signals transmitted in a first time segment.

S420: Determine, based on the plurality of first echo signals, a plurality of first spectrum data groups corresponding to the plurality of first echo signals, where each of the plurality of first spectrum data groups includes a plurality of pieces of first spectrum data, the plurality of pieces of first spectrum data represent a plurality of obstacle points within the first detection range, and each of the plurality of pieces of first spectrum data includes a distance value and a signal strength value; the distance value in each piece of first spectrum data is used to represent a distance between an obstacle point represented by each piece of first spectrum data and a first transmitting origin of the plurality of first radar signals, the signal strength value in each piece of first spectrum data is used to represent reflection strength that is of a first radar signal corresponding to each piece of first spectrum data and that is at the obstacle point represented by each piece of first spectrum data, and a plurality of distance values included in each first spectrum data group are the same.

S430: Perform normalization processing on a signal strength value corresponding to each of the plurality of distance values included in each first spectrum data group, to obtain a normalized signal strength value corresponding to each of the plurality of distance values included in each first spectrum data group.

It should be noted that, for an implementation process of S410 to S430, refer to corresponding descriptions in the method 200. To avoid repetition, details are not described herein.

S440: Determine a first distance between a reference object at a fixed position and the first transmitting origin based on a normalized signal strength value corresponding to a same distance value in the plurality of first spectrum data groups, where the first distance is greater than a distance between a to-be-measured object and the first transmitting origin.

Figure 17:
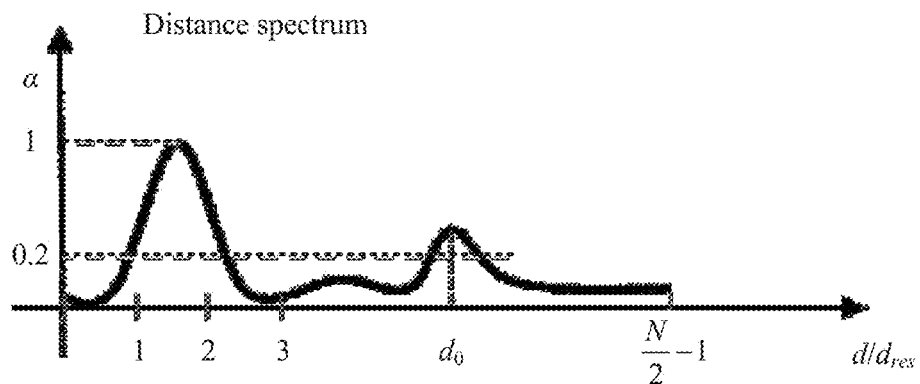
FIG. 17 is a schematic diagram of another Range-FFT according to an embodiment of this application.

FIG. 17 shows the normalized signal strength value, that is, a normalized Range-FFT, corresponding to the same distance value in the plurality of first spectrum data groups. Because an amplitude at each range-bin in the normalized Range-FFT reflects reflection strength that is of a radar signal and that is at an obstacle point, a distance corresponding to a farthest wave peak that is in the normalized Range-FFT and whose amplitude is greater than an amplitude threshold (for example, the amplitude threshold is 0.2) may be considered as the first distance between the reference object and the first transmitting origin.

It should be noted that, in an implementation process of S410 to S440 in the method, the first distance between the reference object and the first transmitting origin is measured, and a detection direction of the first radar signal is from the first transmitting origin to the reference object. Because the first distance is irrelevant to the to-be-measured object, the first radar signal does not need to detect distance information of the to-be-measured object. Therefore, the to-be-measured object may be located at a position far from the first radar signal, or outside the detection range of the first radar signal. This is not limited in this embodiment of this application.

For example, height measurement is used as an example, the first distance may be a distance between a sole of a foot of a to-be-measured person and a ceiling, and a second distance may be a distance between a tot) of a head of the to-be-measured person and the ceiling.

S450: Determine the distance between the to-be-measured object and the first transmitting origin based on the first distance.

Optionally, before S450, a second distance between the reference object and an end that is of the to-be-measured object and that is closest to the reference object may be obtained. The determining the distance between the to-be-measured object and the first transmitting origin based on the first distance includes: determining the distance between the to-be-measured object and the first transmitting origin based on the first distance and the second distance.

In a possible implementation, a plurality of second echo signals generated within a second detection range by a plurality of second radar signals transmitted in a second time segment may be received, where detection directions of the second detection range and the first detection range are opposite. A plurality of second spectrum data groups corresponding to the plurality of second echo signals are determined based on the plurality of second echo signals, where each of the plurality of second spectrum data groups includes a plurality of pieces of second spectrum data, the plurality of pieces of second spectrum data represent a plurality of obstacle points within the second detection range, and each of the plurality of pieces of second spectrum data includes a distance value and a signal strength value. The distance value in each piece of second spectrum data is used to represent a distance between an obstacle point represented by each piece of second spectrum data and a second transmitting origin of the plurality of second radar signals, the signal strength value in each piece of second spectrum data is used to represent reflection strength that is of the plurality of transmitted second radar signals and that is at the obstacle point represented by each piece of second spectrum data, and a plurality of distance values included in each second spectrum data group are the same. Normalization processing is performed on a signal strength value corresponding to each of the plurality of distance values included in each second spectrum data group, to obtain a normalized signal strength value corresponding to each of the plurality of distance values included in each second spectrum data group. The second distance is determined based on a normalized signal strength value corresponding to a same distance value in the plurality of second spectrum data groups.

It should be noted that a principle of a determining process of the second distance is similar to a principle of a determining process of the first distance, and a difference lies only in that the second distance is a distance between the reference object and the end that is of the to-be-measured object and that is closest to the reference object. Therefore, the distance measurement apparatus needs to be placed at the end closest to the reference object. That is, a detection direction of the second radar signal is opposite to the detection direction of the first radar signal, that is, is from the end closest to the reference object to the reference object.

It should be further noted that the method 400 uses the method for improving accuracy of distance measurement described in the method 200 and the method for determining whether there is a to-be-measured object that meets a measurement condition described in the method 200. To avoid repetition, details are not described herein.

According to the distance measurement method provided in this embodiment of this application, distribution of an obstacle in a radar detection range can be better reflected, to facilitate setting of a unified threshold, thereby improving universality of an algorithm and a product.

The foregoing describes the distance measurement methods provided in the embodiments of this application. The following describes, in detail with reference to FIG. 18 to FIG. 21, distance measurement apparatuses provided in the embodiments of this application.

Figure 18:
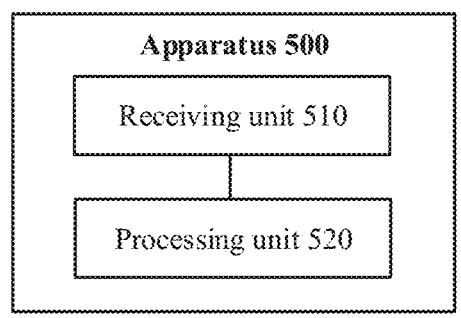
FIG. 18 is a schematic block diagram of a distance measurement apparatus 500 according to an embodiment of this application.

FIG. 18 shows a schematic block diagram of a distance measurement apparatus 500 according to an embodiment of this application. The apparatus 500 includes:

a receiving unit 510, configured to receive a plurality of first echo signals generated within a detection range by a plurality of first radar signals transmitted in a first time segment; and a processing unit 520, configured to determine a first point cloud dataset based on the plurality of first echo signals, where the first point cloud dataset includes a plurality of pieces of first point cloud data, the plurality of pieces of first point cloud data are used to represent a plurality of obstacle points on a to-be-measured object within the detection range, and each of the plurality of pieces of first point cloud data includes a distance value, a rate value, and a signal-to-noise ratio value; the distance value in each piece of first point cloud data is used to represent a distance between an obstacle point represented by each piece of first point cloud data and a transmitting origin of the plurality of first radar signals, the rate value in each piece of first point cloud data is used to represent a motion rate that is of the obstacle point represented by each piece of first point cloud data and that is relative to the transmitting origin, and the signal-to-noise ratio value in each piece of first point cloud data is used to represent noise at the obstacle point represented by each piece of first point cloud data; perform denoising on the first point cloud dataset based on the signal-to-noise ratio value and the rate value that are in each piece of first point cloud data included in the first point cloud dataset, to obtain a target dataset; cluster, based on a distance value in each piece of first point cloud data included in the target dataset, first point cloud data included in the target dataset, to obtain at least one classification, where the at least one classification corresponds to at least one obstacle, and an obstacle point included in each of the at least one classification forms an obstacle corresponding to each classification; and determine a distance between the obstacle corresponding to each classification and the transmitting origin based on a distance value in each piece of first point cloud data included in each classification.

Optionally, the processing unit 520 is specifically configured to perform denoising on the first point cloud dataset based on the signal-to-noise ratio value and the rate value that are in each piece of first point cloud data included in the first point cloud dataset, a preset signal-to-noise ratio threshold, and a preset rate threshold, to obtain the target dataset, where the rate threshold is determined based on a rate of a target obstacle in the at least one obstacle.

Optionally, the rate of the target obstacle is greater than or equal to the rate threshold.

Optionally, the target obstacle includes a first obstacle point and a second obstacle point, and a distance between the first obstacle point and the second obstacle point is less than a preset distance threshold.

Optionally, the target obstacle corresponds to a target classification in the at least one classification, and the processing unit 520 is specifically configured to determine a classification that includes a largest amount of first point cloud data in the at least one classification as the target classification; and determine a distance between the target obstacle and the transmitting origin based on a distance value in each piece of first point cloud data included in the target classification.

Optionally, the distance value in each piece of first point cloud data includes a distance component value in a first direction and a distance component value in a second direction that are of the obstacle point represented by each piece of first point cloud data, where the first direction is perpendicular to the second direction: or the distance value in each piece of first point cloud data includes the distance component value in the first direction, the distance component value in the second direction, and a distance component value in a third direction that are of the obstacle point represented by each piece of first point cloud data, where the third direction is separately perpendicular to the first direction and the second direction.

Optionally, the processing unit 520 is specifically configured to determine, based on the plurality of first echo signals, a plurality of first spectrum data groups corresponding to the plurality of first echo signals, where each of the plurality of first spectrum data groups includes a plurality of pieces of first spectrum data, the plurality of pieces of first spectrum data represent the plurality of obstacle points within the detection range, and each of the plurality of pieces of first spectrum data includes a distance value and a signal strength value; the distance value in each piece of first spectrum data is used to represent a distance between an obstacle point represented by each piece of first spectrum data and the transmitting origin, the signal strength value in each piece of first spectrum data is used to represent reflection strength that is of a first radar signal corresponding to each piece of first spectrum data and that is at the obstacle point represented by each piece of first spectrum data, and a plurality of distance values included in each first spectrum data group are the same; and determine the first point cloud dataset based on the distance value and the signal strength value that are in each piece of first spectrum data.

Optionally, the receiving unit 510 is further configured to: before the determining the first point cloud dataset based on the distance value and the signal strength value that are in each piece of first spectrum data, receive a plurality of second echo signals generated within the detection range by a plurality of second radar signals transmitted in a second time segment, where an end time point of the second time segment is not later than an end time point of the first time segment. The processing unit 520 is further configured to determine, based on the plurality of second echo signals, a plurality of second spectrum data groups corresponding to the plurality of second echo signals, where each of the plurality of second spectrum data groups includes a plurality of pieces of second spectrum data, the plurality of pieces of second spectrum data represent the plurality of obstacle points within the detection range, and each of the plurality of pieces of second spectrum data includes a distance value and a signal strength value; the distance value in each piece of second spectrum data is used to represent a distance between an obstacle point represented by each piece of second spectrum data and the transmitting origin, the signal strength value in each piece of second spectrum data is used to represent reflection strength that is of a second radar signal corresponding to each piece of second spectrum data and that is at the obstacle point represented by each piece of second spectrum data, and a plurality of distance values included in each second spectrum data group are the same; determine, based on the distance value and the signal strength value that are in each piece of second spectrum data, whether a position of the to-be-measured object meets a measurement condition; and determine the first point cloud dataset when determining that the position of the to-be-measured object meets the measurement condition.

Optionally the processing unit 520 is further configured to perform normalization processing on a signal strength value corresponding to each of the plurality of distance values included in each second spectrum data group, to obtain a normalized signal strength value corresponding to each of the plurality of distance values included in each second spectrum data group; determine, based on a normalized signal strength value corresponding to a same distance value in the plurality of second spectrum data groups, a variance value of a signal strength value corresponding to each of the plurality of distance values; and determine, based on the variance value of the signal strength value corresponding to each of the plurality of distance values, whether the position of the to-be-measured object meets the measurement condition.

Optionally, the processing unit 520 is specifically configured to: when a quantity of variance values that are greater than a variance threshold and that are of signal strength values corresponding to all of the plurality of distance values is greater than or equal to a quantity threshold, determine that the position of the to-be-measured object meets the measurement condition; or when the quantity of variance values that are greater than the variance threshold and that are of signal strength values corresponding to all of the plurality of distance values is less than the quantity threshold, determine that the position of the to-be-measured object does not meet the measurement condition.

It should be understood that the apparatus 500 herein is embodied in a form of a functional unit. The term "unit" herein may be an application-specific integrated circuit (ASIC), an electronic circuit, a processor (for example, a shared processor, a dedicated processor, or a group processor) configured to execute one or more software or firmware programs, a memory, a merged logic circuit, and/or another proper component that supports the described functions. In an optional example, a person skilled in the art may understand that the apparatus 500 may be specifically the distance measurement apparatus in the foregoing embodiment of the method 200, and the apparatus 500 may be configured to perform procedures and/or steps corresponding to the distance measurement apparatus in the method 200. To avoid repetition, details are not described herein.

Figure 19:
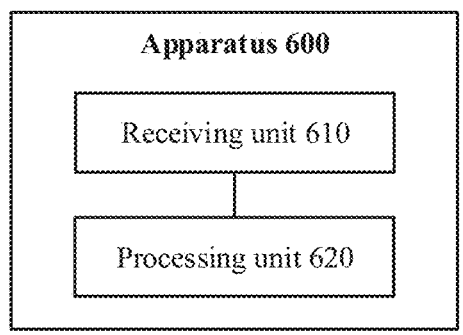
FIG. 19 is a schematic block diagram of a distance measurement apparatus 600 according to an embodiment of this application.

FIG. 19 shows a schematic block diagram of a distance measurement apparatus 600 according to an embodiment of this application. The apparatus 600 includes:

a receiving unit 610, configured to receive a plurality of first echo signals generated within a detection range by a plurality of first radar signals transmitted in a first time segment; and a processing unit 620, configured to determine, based on the plurality of first echo signals, a plurality of first spectrum data groups corresponding to the plurality of first echo signals, where each of the plurality of first spectrum data groups includes a plurality of pieces of first spectrum data, the plurality of pieces of first spectrum data represent a plurality of obstacle points on a to-be-measured object within the detection range, and each of the plurality of pieces of first spectrum data includes a distance value and a signal strength value, the distance value in each piece of first spectrum data is used to represent a distance between an obstacle point represented by each piece of first spectrum data and a transmitting origin of the plurality of first radar signals, the signal strength value in each piece of first spectrum data is used to represent signal reflection strength at the obstacle point represented by each piece of first spectrum data, and a plurality of distance values included in each first spectrum data group are the same; perform normalization processing on a signal strength value corresponding to each distance value included in each first spectrum data group, to obtain a normalized signal strength value corresponding to each distance value included in each first spectrum data group; determine, based on a normalized signal strength value corresponding to a same distance value in the plurality of first spectrum data groups, a variance value of a signal strength value corresponding to each distance value included in the plurality of first spectrum data groups; and determine a distance between a target obstacle on the to-be-measured object and the transmitting origin based on the variance value of the signal strength value corresponding to each distance value included in the plurality of first spectrum data groups, where the target obstacle includes at least one obstacle point, and signal reflection strength at obstacle points in different motion statuses is different.

Optionally, the processing unit 620 is specifically configured to determine the distance between the target obstacle and the transmitting origin based on the variance value of the signal strength value corresponding to each distance value included in the plurality of first spectrum data groups and a first variance threshold, where the first variance threshold is determined based on signal strength at the at least one obstacle point that forms the target obstacle.

Optionally, the receiving unit 610 is further configured to: before the performing normalization processing on a signal strength value corresponding to each distance value included in each first spectrum data group, to obtain a normalized signal strength value corresponding to each distance value included in each first spectrum data group, receive a plurality of second echo signals generated within the detection range by a plurality of second radar signals transmitted in a second time segment, where an end time point of the second time segment is not later than an end time point of the first time segment. The processing unit 620 is further configured to determine, based on the plurality of second echo signals, a plurality of second spectrum data groups corresponding to the plurality of second echo signals, where each of the plurality of second spectrum data groups includes a plurality of pieces of second spectrum data, the plurality of pieces of second spectrum data represent the plurality of obstacle points within the detection range, and each of the plurality of pieces of second spectrum data includes a distance value and a signal strength value; the distance value in each piece of second spectrum data is used to represent a distance between an obstacle point represented by each piece of second spectrum data and the transmitting origin, the signal strength value in each piece of second spectrum data is used to represent signal reflection strength at the obstacle point represented by each piece of second spectrum data, and a plurality of distance values included in each second spectrum data group are the same; and determine, based on the distance value and the signal strength value that are in each piece of second spectrum data, whether a position of the to-be-measured object meets a measurement condition. The processing unit 620 is specifically configured to: when determining that the position of the to-be-measured object meets the measurement condition, perform normalization processing on the signal strength value corresponding to each distance value included in each first spectrum data group.

Optionally, the processing unit 620 is further configured to perform normalization processing on a signal strength value corresponding to each distance value included in each second spectrum data group, to obtain a normalized signal strength value corresponding to each distance value included in each second spectrum data group; determine, based on a normalized signal strength value corresponding to a same distance value in the plurality of second spectrum data groups, a variance value of a signal strength value corresponding to each distance value included in the plurality of second spectrum data groups; and determine, based on the variance value of the signal strength value corresponding to each distance value included in the plurality of second spectrum data groups, whether the position of the to-be-measured object meets the measurement condition.

Optionally, the processing unit 620 is specifically configured to: when a quantity of variance values that are greater than a second variance threshold and that are of signal strength values corresponding to all distance values included in the plurality of second spectrum data groups is greater than or equal to a quantity threshold, determine that the position of the to-be-measured object meets the measurement condition; or when the quantity of variance values that are greater than the second variance threshold and that are of signal strength values corresponding to all distance values included in the plurality of second spectrum data groups is less than the quantity threshold, determine that the position of the to-be-measured object does not meet the measurement condition.

It should be understood that the apparatus 600 herein is embodied in a form of a functional unit. The term "unit" herein may be an ASIC, an electronic circuit, a processor (for example, a shared processor, a dedicated processor, or a group processor) configured to execute one or more software or firmware programs, a memory, a merged logic circuit, and/or another proper component that supports the described functions. In an optional example, a person skilled in the art may understand that the apparatus 600 may be specifically the distance measurement apparatus in the foregoing embodiment of the method 300, and the apparatus 600 may be configured to perform procedures and/or steps corresponding to the distance measurement apparatus in the method 300. To avoid repetition, details are not described herein.

Figure 20:
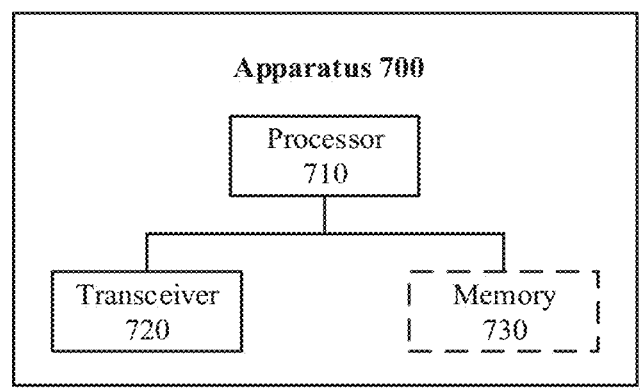
FIG. 20 is a schematic block diagram of a distance measurement apparatus 700 according to an embodiment of this application.

FIG. 20 shows a distance measurement apparatus 700 according to an embodiment of this application. The apparatus 700 may be the apparatus 500 in FIG. 18, or the apparatus 700 may include the apparatus 500 in FIG. 18. The apparatus 500 may use a hardware architecture shown in FIG. 20. The apparatus 700 may include a processor 710 and a transceiver 720, and the processor 710 and the transceiver 720 communicate with each other by using an internal connection path. A related function implemented by the processing unit 520 in FIG. 18 may be implemented by the processor 710, and a related function implemented by the receiving unit 510 may be implemented by the transceiver 720 under control of the processor 710.

The processor 710 may include one or more processors, for example, include one or more central processing units (CPUs). When the processor is one CPU, the CPU may be a single-core CPU or a multi-core CPU.

The transceiver 720 is configured to send and receive signals. The transceiver may include a transmitter and a receiver, the transmitter is configured to send a radar signal, and the receiver is configured to receive a radar signal.

Optionally, the apparatus 700 may further include a memory 730. The processor 710, the transceiver 720, and the memory 730 communicate with each other by using an internal connection path.

The memory 730 includes but is not limited to a random access memory (RAM), a read-only memory (ROM), an erasable programmable read-only memory (EPROM), and a compact disc read-only memory (CD-ROM). The memory 730 is configured to store related instructions and data.

The memory 730 is configured to store program code and data of the apparatus, and may be an independent component or integrated into the processor 710.

Specifically, the processor 710 is configured to control the transceiver 720 to transmit a radar signal and receive an echo signal. For details, refer to the descriptions in the method embodiments. Details are not described herein again.

It may be understood that FIG. 20 merely shows a simplified design of the apparatus 700. In actual application, the apparatus 700 may further include another necessary element, including but not limited to any quantity of transceivers, processors, controllers, memories, and the like. All measurement devices that can implement this application fall within the protection scope of this application.

In a possible design, the apparatus 700 may be replaced with a chip apparatus, configured to implement the related function of the processor in the apparatus. The chip apparatus may be a field programmable gate array, a dedicated integrated chip, a system chip, a central processing unit, a network processor, a digital signal processing circuit, a microcontroller, a programmable controller, or another integrated chip for implementing related functions. Optionally, the chip may include one or more memories, configured to store program code. When the code is executed, the processor is enabled to implement a corresponding function.

Figure 21:
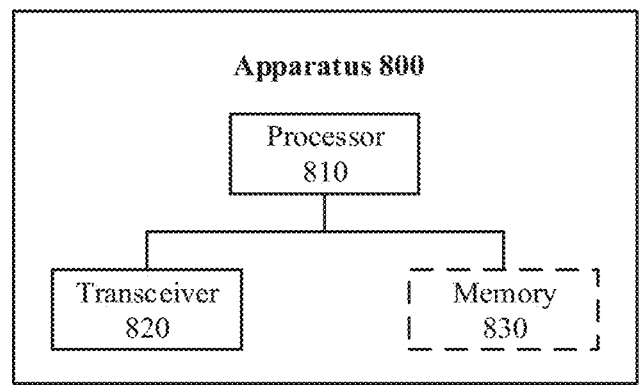
FIG. 21 is a schematic block diagram of a distance measurement apparatus 800 according to an embodiment of this application.

FIG. 21 shows a distance measurement apparatus 800 according to an embodiment of this application. The apparatus 800 may be the apparatus 600 in FIG. 19, or the apparatus 800 may include the apparatus 600 in FIG. 19. The apparatus 600 may use a hardware architecture shown in FIG. 21. The apparatus 800 may include a processor 810 and a transceiver 820, and the processor 810 and the transceiver 820 communicate with each other by using an internal connection path. A related function implemented by the processing unit 620 in FIG. 19 may be implemented by the processor 810, and a related function implemented by the receiving unit 610 may be implemented by the transceiver 820 under control of the processor 810.

The processor 810 may include one or more processors, for example, include one or more CPUs. When the processor is one CPU, the CPU may be a single-core CPU or a multi-core CPU.

The transceiver 820 is configured to send and receive signals. The transceiver may include a transmitter and a receiver, the transmitter is configured to send a radar signal, and the receiver is configured to receive a radar signal.

Optionally, the apparatus 800 may further include a memory 830. The processor 810, the transceiver 820, and the memory 830 communicate with each other by using an internal connection path.

The memory 830 includes but is not limited to a RAM, a ROM, an EPROM, and a CD-ROM. The memory 830 is configured to store related instructions and data.

The memory 830 is configured to store program code and data of the apparatus, and may be an independent component or integrated into the processor 810.

Specifically, the processor 810 is configured to control the transceiver to transmit a radar signal and receive an echo signal. For details, refer to the descriptions in the method embodiments. Details are not described herein again.

It may be understood that FIG. 21 merely shows a simplified design of the apparatus 800. In actual application, the apparatus 800 may further include another necessary element, including but not limited to any quantity of transceivers, processors, controllers, memories, and the like. All measurement devices that can implement this application fall within the protection scope of this application.

In a possible design, the apparatus 800 may be replaced with a chip apparatus, configured to implement the related function of the processor in the apparatus. The chip apparatus may be a field programmable gate array, a dedicated integrated chip, a system chip, a central processing unit, a network processor, a digital signal processing circuit, a microcontroller, a programmable controller, or another integrated chip for implementing related functions. Optionally, the chip may include one or more memories, configured to store program code. When the code is executed, the processor is enabled to implement a corresponding function.

It should be understood that sequence numbers of the foregoing processes do not mean execution sequences in the embodiments of this application. The execution sequences of the processes should be determined according to functions and internal logic of the processes, and should not be construed as any limitation on the implementation processes of the embodiments of this application.

A person of ordinary skill in the art may be aware that, in combination with the examples described in the embodiments disclosed in this specification, units and algorithm steps can be implemented by electronic hardware or a combination of computer software and electronic hardware. Whether the functions are performed by hardware or software depends on particular applications and design constraints of the technical solutions. A person skilled in the art may use different methods to implement the described functions of each particular application, but it should not be considered that the implementation goes beyond the scope of this application.

A person skilled in the art may clearly understand that, for the purpose of convenient and brief description, for a detailed working process of the foregoing system, apparatus, and unit, refer to a corresponding process in the foregoing method embodiments, and details are not described herein again.

In the several embodiments provided in this application, it should be understood that the disclosed systems, apparatuses, and methods may be implemented in other manners. For example, the described apparatus embodiments are merely examples. For example, division into units is merely logical function division and may be other division during actual implementation. For example, a plurality of units or components may be combined or integrated into another system, or some features may be ignored or not performed. In addition, the displayed or discussed mutual couplings or direct couplings or communication connections may be implemented through some interfaces. The indirect couplings or communication connections between the apparatuses or the units may be implemented in electronic, mechanical, or other forms.

The units described as separate parts may or may not be physically separate, and parts displayed as units may or may not be physical units, may be located in one position, or may be distributed on a plurality of network units. Some or all of the units may be selected based on actual requirements to achieve the objectives of the solutions of the embodiments.

In addition, functional units in the embodiments of this application may be integrated into one processing unit, or each of the units may exist alone physically, or two or more units may be integrated into one unit.

When the functions are implemented in a form of a software functional unit and sold or used as an independent product, the functions may be stored in a computer-readable storage medium. Based on such an understanding, the technical solutions of this application essentially, or the part contributing to the current technology, or some of the technical solutions may be implemented in a form of a computer software product. The computer software product is stored in a storage medium, and includes several instructions for instructing a computer device (which may be a personal computer, a server, or a network device) to perform all or some of the steps of the methods described in the embodiments of this application. The foregoing storage medium includes any medium that can store program code, for example, a USB flash drive, a removable hard disk, a ROM, a RAM, a magnetic disk, or an optical disc.

The foregoing descriptions are merely specific implementations of this application, but are not intended to limit the protection scope of this application. Any variation or replacement readily figured out by a person skilled in the art within the technical scope disclosed in this application shall fall within the protection scope of this application. Therefore, the protection scope of this application shall be subject to the protection scope of the claims.

What is claimed is:

1. A distance measurement method, comprising:
   receiving a plurality of first echo signals generated within a detection range by a plurality of first radar signals transmitted in a first time segment;
   determining, based on the plurality of first echo signals, a plurality of first spectrum data groups corresponding to the plurality of first echo signals, wherein each of the plurality of first spectrum data groups comprises a plurality of pieces of first spectrum data representing a plurality of obstacle points on a to-be-measured object within the detection range, each of the plurality of pieces of first spectrum data comprises a distance value and a signal strength value, the distance value in each piece of the plurality of pieces of first spectrum data represents a distance between an obstacle point represented by each piece of the plurality of pieces of first spectrum data and a transmitting origin of the plurality of first radar signals, the signal strength value in each piece of the plurality of pieces of first spectrum data represents signal reflection strength at the obstacle point represented by each piece of the plurality of pieces of first spectrum data, and a plurality of distance values comprised in each of the plurality of first spectrum data groups are the same;
   performing normalization processing on a signal strength value corresponding to each distance value comprised in each of the plurality of first spectrum data groups to obtain a normalized signal strength value corresponding to each distance value comprised in each of the plurality of first spectrum data groups;
   determining, based on a normalized signal strength value corresponding to a same distance value in the plurality of first spectrum data groups, a variance value of a signal strength value corresponding to each distance value comprised in the plurality of first spectrum data groups; and
   determining a distance between a target obstacle on the to-be-measured object and the transmitting origin based on the variance value of the signal strength value corresponding to each distance value comprised in the plurality of first spectrum data groups, wherein the target obstacle comprises at least one obstacle point, and signal reflection strength at obstacle points in different motion statuses are different.

2. The method according to claim 1, wherein determining the distance between the target obstacle on the to-be-measured object and the transmitting origin comprises:
   determining the distance between the target obstacle and the transmitting origin based on the variance value of the signal strength value corresponding to each distance value comprised in the plurality of first spectrum data groups and a first variance threshold, wherein the first variance threshold is determined based on signal strength at the at least one obstacle point that forms the target obstacle.

3. The method according to claim 1, wherein the method further comprises:
before performing the normalization processing, receiving a plurality of second echo signals generated within the detection range by a plurality of second radar signals transmitted in a second time segment, wherein an end time point of the second time segment is not later than an end time point of the first time segment;
determining, based on the plurality of second echo signals, a plurality of second spectrum data groups corresponding to the plurality of second echo signals, wherein each of the plurality of second spectrum data groups comprises a plurality of pieces of second spectrum data representing the plurality of obstacle points within the detection range, each of the plurality of pieces of second spectrum data comprises a distance value and a signal strength value, the distance value in each piece of second spectrum data represents a distance between an obstacle point represented by each piece of second spectrum data and the transmitting origin, the signal strength value in each piece of second spectrum data represents signal reflection strength at the obstacle point represented by each piece of second spectrum data, and a plurality of distance values comprised in each second spectrum data group are the same;
determining, based on the distance value and the signal strength value that are in each piece of second spectrum data, whether a position of the to-be-measured object meets a measurement condition; and
in response to determining that the position of the to-be-measured object meets the measurement condition, performing normalization processing on the signal strength value corresponding to each distance value comprised in each of the plurality of first spectrum data groups.

4. The method according to claim 3, wherein determining whether the position of the to-be-measured object meets the measurement condition comprises:
performing normalization processing on a signal strength value corresponding to each distance value comprised in each second spectrum data group to obtain a normalized signal strength value corresponding to each distance value comprised in each second spectrum data group;
determining, based on a normalized signal strength value corresponding to a same distance value in the plurality of second spectrum data groups, a variance value of a signal strength value corresponding to each distance value comprised in the plurality of second spectrum data groups; and
determining, based on the variance value of the signal strength value corresponding to each distance value comprised in the plurality of second spectrum data groups, whether the position of the to-be-measured object meets the measurement condition.

5. The method according to claim 4, wherein determining whether the position of the to-be-measured object meets the measurement condition comprises:
in response to determining that a quantity of variance values, greater than a second variance threshold, of signal strength values corresponding to all distance values comprised in the plurality of second spectrum data groups is greater than or equal to a quantity threshold, determining that the position of the to-be-measured object meets the measurement condition; or
in response to determining that the quantity of variance values, greater than the second variance threshold, of signal strength values corresponding to all distance values comprised in the plurality of second spectrum data groups is less than the quantity threshold, determining that the position of the to-be-measured object does not meet the measurement condition.

6. A distance measurement apparatus, comprising at least one processor, a memory, and a transceiver, wherein the at least one processor is coupled to the transceiver, and the memory stores programming instructions for execution by the at least one processor to perform operations comprising:
receiving a plurality of first echo signals generated within a detection range by a plurality of first radar signals transmitted in a first tire segment;
determining, based on the plurality of first echo signals, a plurality of first spectrum data groups corresponding to the plurality of first echo signals, wherein each of the plurality of first spectrum data groups comprises a plurality of pieces of first spectrum data representing a plurality of obstacle points on a to-be-measured object within the detection range, each of the plurality of pieces of first spectrum data comprises a distance value and a signal strength value, the distance value in each piece of the plurality of pieces of first spectrum data represents a distance between an obstacle point represented by each piece of the plurality of pieces of first spectrum data and a transmitting origin of the plurality of first radar signals, the signal strength value in each piece of the plurality of pieces of first spectrum data represents signal reflection strength at the obstacle point represented by each piece of the plurality of pieces of first spectrum data, and a plurality of distance values comprised in each of the plurality of first spectrum data groups are the same;
performing normalization processing on a signal strength value corresponding to each distance value comprised in each of the plurality of first spectrum data groups to obtain a normalized signal strength value corresponding to each distance value comprised in each of the plurality of first spectrum data groups;
determining, based on a normalized signal strength value corresponding to a same distance value in the plurality of first spectrum data groups, a variance value of a signal strength value corresponding to each distance value comprised in the plurality of first spectrum data groups; and
determining a distance between a target obstacle on the to-be-measured object and the transmitting origin based on the variance value of the signal strength value corresponding to each distance value comprised in the plurality of first spectrum data groups, wherein the target obstacle comprises at least one obstacle point, and signal reflection strength at obstacle points in different motion statuses are different.

7. The apparatus according to claim 6, wherein determining the distance between the target obstacle on the to-be-measured object and the transmitting origin comprises:
determining the distance between the target obstacle and the transmitting origin based on the variance value of the signal strength value corresponding to each distance value comprised in the plurality of first spectrum data groups and a first variance threshold, wherein the first variance threshold is determined based on signal strength at the at least one obstacle point that forms the target obstacle.

8. The apparatus according to claim 6, wherein the operations further comprise:
receiving a plurality of second echo signals generated within the detection range by a plurality of second radar signals transmitted in a second time segment, wherein an end time point of the second time segment is not later than an end time point of the first time segment;
determining, based on the plurality of second echo signals, a plurality of second spectrum data groups corresponding to the plurality of second echo signals, wherein each of the plurality of second spectrum data groups comprises a plurality of pieces of second spectrum data representing the plurality of obstacle points within the detection range, each of the plurality of pieces of second spectrum data comprises a distance value and a signal strength value, the distance value in each piece of second spectrum data represents a distance between an obstacle point represented by each piece of second spectrum data and the transmitting origin, the signal strength value in each piece of second spectrum data represents signal reflection strength at the obstacle point represented by each piece of second spectrum data, and a plurality of distance values comprised in each second spectrum data group are the same;
determining, based on the distance value and the signal strength value that are in each piece of second spectrum data, whether a position of the to-be-measured object meets a measurement condition; and
in response to determining that the position of the to-be-measured object meets the measurement condition, performing normalization processing on the signal strength value corresponding to each distance value comprised in each of the plurality of first spectrum data groups.

9. The apparatus according to claim 8, wherein the operations comprise:
performing normalization processing on a signal strength value corresponding to each distance value comprised in each second spectrum data group to obtain a normalized signal strength value corresponding to each distance value comprised in each second spectrum data group;
determining, based on a normalized signal strength value corresponding to a same distance value in the plurality of second spectrum data groups, a variance value of a signal strength value corresponding to each distance value comprised in the plurality of second spectrum data groups; and
determining, based on the variance value of the signal strength value corresponding to each distance value comprised in the plurality of second spectrum data groups, whether the position of the to-be-measured object meets the measurement condition.

10. The apparatus according to claim 9, wherein the operations comprise:
in response to determining that a quantity of variance values, greater than a second variance threshold, of signal strength values corresponding to all distance values comprised in the plurality of second spectrum data groups is greater than or equal to a quantity threshold, determining that the position of the to-be-measured object meets the measurement condition; or in response to determining that the quantity of variance values, greater than the second variance threshold, of signal strength values corresponding to all distance values comprised in the plurality of second spectrum data groups is less than the quantity threshold, determining that the position of the to-be-measured object does not meet the measurement condition.

11. A non-transitory computer-readable storage medium, wherein the non-transitory computer-readable storage medium stores program code which, when executed by a device, causes the devise to perform operations comprising:
receiving a plurality of first echo signals generated within a detection range by a plurality of first radar signals transmitted in a first time segment;
determining, based on the plurality of first echo signals, a plurality of first spectrum data groups corresponding to the plurality of first echo signals, wherein each of the plurality of first spectrum data groups comprises a plurality of pieces of first spectrum data representing a plurality of obstacle points on a to-be-measured object within the detection range, each of the plurality of pieces of first spectrum data comprises a distance value and a signal strength value, the distance value in each piece of the plurality of pieces of first spectrum data represents a distance between an obstacle point represented by each piece of the plurality of pieces of first spectrum data and a transmitting origin of the plurality of first radar signals, the signal strength value in each piece of the plurality of pieces of first spectrum data represents signal reflection strength at the obstacle point represented by each piece of the plurality of pieces of first spectrum data, and a plurality of distance values comprised in each of the plurality of first spectrum data groups are the same;
performing normalization processing on a signal strength value corresponding to each distance value comprised in each of the plurality of first spectrum data groups to obtain a normalized signal strength value corresponding to each distance value comprised in each of the plurality of first spectrum data groups;
determining, based on a normalized signal strength value corresponding to a same distance value in the plurality of first spectrum data groups, a variance value of a signal strength value corresponding to each distance value comprised in the plurality of first spectrum data groups; and
determining a distance between a target obstacle on the to-be-measured object and the transmitting origin based on the variance value of the signal strength value corresponding to each distance value comprised in the plurality of first spectrum data groups, wherein the target obstacle comprises at least one obstacle point, and signal reflection strength at obstacle points in different motion statuses are different.

12. The non-transitory computer-readable storage medium according to claim 11, wherein determining the distance between the target obstacle on the to-be-measured object and the transmitting origin comprises:
determining the distance between the target obstacle and the transmitting origin based on the variance value of the signal strength value corresponding to each distance value comprised in the plurality of first spectrum data groups and a first variance threshold, wherein the first variance threshold is determined based on signal strength at the at least one obstacle point that forms the target obstacle.

13. The non-transitory computer-readable storage medium according to claim 11, wherein the operations further comprise:
- receiving a plurality of second echo signals generated within the detection range by a plurality of second radar signals transmitted in a second time segment, wherein an end time point of the second time segment is not later than an end time point of the first time segment;
- determining, based on the plurality of second echo signals, a plurality of second spectrum data groups corresponding to the plurality of second echo signals, wherein each of the plurality of second spectrum data groups comprises a plurality of pieces of second spectrum data representing the plurality of obstacle points within the detection range, each of the plurality of pieces of second spectrum data comprises a distance value and a signal strength value, the distance value in each piece of second spectrum data represents a distance between an obstacle point represented by each piece of second spectrum data and the transmitting origin, the signal strength value in each piece of second spectrum data represents signal reflection strength at the obstacle point represented by each piece of second spectrum data, and a plurality of distance values comprised in each second spectrum data group are the same;
- determining, based on the distance value and the signal strength value that are in each piece of second spectrum data, whether a position of the to-be-measured object meets a measurement condition; and
- in response to determining that the position of the to-be-measured object meets the measurement condition, performing normalization processing on the signal strength value corresponding to each distance value comprised in each of the plurality of first spectrum data groups.

14. The non-transitory computer-readable storage medium according to claim 13, wherein the operations comprise:
- performing normalization processing on a signal strength value corresponding to each distance value comprised in each second spectrum data group, to obtain a normalized signal strength value corresponding to each distance value comprised in each second spectrum data group;
- determining, based on a normalized signal strength value corresponding to a same distance value in the plurality of second spectrum data groups, a variance value of a signal strength value corresponding to each distance value comprised in the plurality of second spectrum data groups; and
- determining, based on the variance value of the signal strength value corresponding to each distance value comprised in the plurality of second spectrum data groups, whether the position of the to-be-measured object meets the measurement condition.

15. The non-transitory computer-readable storage medium according to claim 14, wherein the operations comprise:
- in response to determining that a quantity of variance values, greater than a second variance threshold, of signal strength values corresponding to all distance values comprised in the plurality of second spectrum data groups is greater than or equal to a quantity threshold, determining that the position of the to-be-measured object meets the measurement condition; or
- in response to determining that the quantity of variance values, greater than the second variance threshold, of signal strength values corresponding to all distance values comprised in the plurality of second spectrum data groups is less than the quantity threshold, determining that the position of the to-be-measured object does not meet the measurement condition.

* * * * *

UNITED STATES PATENT AND TRADEMARK OFFICE
CERTIFICATE OF CORRECTION

| | |
|---|---|
| PATENT NO. | : 12,146,937 B2 |
| APPLICATION NO. | : 17/842931 |
| DATED | : November 19, 2024 |
| INVENTOR(S) | : Genming Ding and Yanong He |

It is certified that error appears in the above-identified patent and that said Letters Patent is hereby corrected as shown below:

In the Claims

In Column 38, In Line 18, In Claim 6, delete "tire" and insert -- time --.

In Column 40, In Line 12 (Approx.), In Claim 11, delete "devise" and insert -- device --.

Signed and Sealed this
Fourth Day of March, 2025

Coke Morgan Stewart
*Acting Director of the United States Patent and Trademark Office*